US009012152B2

(12) United States Patent
Engelberg-Kulka et al.

(10) Patent No.: US 9,012,152 B2
(45) Date of Patent: Apr. 21, 2015

(54) ANTI-BACTERIAL PEPTIDES AND METHODS OF TREATING DISEASES USING SAME

(75) Inventors: Hanna Engelberg-Kulka, Jerusalem (IL); Ilana Kolodkin-Gal, Jerusalem (IL)

(73) Assignee: Yissum Research Development Company of the Hebrew University of Jerusalem, Jerusalem (IL)

( * ) Notice: Subject to any disclaimer, the term of this patent is extended or adjusted under 35 U.S.C. 154(b) by 768 days.

(21) Appl. No.: 12/522,545

(22) PCT Filed: Jan. 8, 2008

(86) PCT No.: PCT/IL2008/000039
§ 371 (c)(1),
(2), (4) Date: Dec. 11, 2009

(87) PCT Pub. No.: WO2008/084478
PCT Pub. Date: Jul. 17, 2008

(65) Prior Publication Data
US 2010/0104607 A1 Apr. 29, 2010

Related U.S. Application Data

(60) Provisional application No. 60/879,343, filed on Jan. 9, 2007.

(51) Int. Cl.
*G01N 33/53* (2006.01)
*G01N 33/569* (2006.01)
*C07K 14/245* (2006.01)

(52) U.S. Cl.
CPC .................................. *C07K 14/245* (2013.01)

(58) Field of Classification Search
None
See application file for complete search history.

(56) References Cited

U.S. PATENT DOCUMENTS 7,820,624 B2 * 10/2010 Hart et al. .................... 514/1.2
2005/0267028 A1 12/2005 Virji

FOREIGN PATENT DOCUMENTS

WO   WO 00/15660    3/2000
WO   WO 2004/042059  5/2004

OTHER PUBLICATIONS

Prozorov et al. Toxin-Antitoxin Systems in Bacteria: Apoptotic Tools or Metabolic Regulators? Microbiology, 2010, vol. 79, No. 2, pp. 129-140.*
Wood and Wisniewski. 1-Lactams versus Glycopeptides in Treatment of Subcutaneous Abscesses Infected with *Staphylococcus aureus*. Antimicrobial Agents and Chemotherapy, May 1994, p. 1023-1026.*
Gottler and Ramamoorthy. Structure, membrane orientation, mechanism, and function of pexiganan—A highly potent antimicrobial peptide designed from magainin. Biochimica et Biophysica Acta (BBA)—Biomembranes vol. 1788, Issue 8, Aug. 2009, pp. 1680-1686.*
Communication Relating to the Results of the Partial International Search Dated May 23, 2008 From the International Searching Authority Re.: Application No. PCT/IL2008/000039.
Engelberg-Kulka et al. "Bacterial Programmed Cell Death Systems as Targets for Antibiotics", Trends in Microbiology, XP002477942, 12(2): 66-71, Feb. 2004. p. 67, 1-h Col., Last §-p. 68, r-h Col., § 2.
Kolodkin-Gal et al. "A Linear Pentapeptide Is a Quorum-Sensing Factor Required for MazEF-Mediated Cell Death in *Escherichia coli*", Science, XP002477943, 318: 652-655, Oct. 26, 2007.
Miyasaki et al. "Bactericidal Activities of Synthetic Human Leukocyte Cathepsin G-Derived Antibiotic Peptides and Congeners Against *Actinobacillus actinomycetemcomitans* and *Capocytophaga sputigena*", Antimicrobial Agents and Chemotherapy, XP002477940, 37(12): 2710-2715, Dec. 1993. Tables 1, 2.
Noting of Loss of Rights Pursuant to Rule 112(1) EPC Dated Feb. 22, 2011 From the European Patent Office Re. Application No. 08702621.7.
Response Dated Mar. 9, 2011 to Noting of Loss of Rights Pursuant to Rule 112(1) EPC of Feb. 22, 2011 From the European Patent Office Re. Application No. 08702621.7.
López-Expósito et al. "Identification of Antibacterial Peptides From Ovine αS2-Casein", International Dairy Journal, XP002477939, 16(9): 1072-1080, 2006.
Communication Pursuant to Article 94(3) EPC Dated Sep. 6, 2010 From the European Patent Office Re. Application No. 08702621.7.
International Search Report and the Written Opinion Dated Jul. 23, 2008 From the International Searching Authority Re.: Application No. PCT/IL2008/000039.
Li et al. "Type I β-Turn Conformation Is Important for Biological Activity of the Melanocyte-Stimulating Hormone Analogues", European Journal of Biochemistry, XP002477941, 265(1): 430-440, 1999. Table 1.
López-Expósito et al. "Identification of Antibacterial Peptides From Ovine αS2-Casein", International Dairy Journal, XP002477939, 16(9): 1072-1080, 2006. Tables 1, 2.

* cited by examiner

*Primary Examiner* — Maher Haddad

(57) ABSTRACT

Isolated peptides comprising no more than ten amino acids and having anti-bacterial properties are disclosed. In one embodiment the peptides have a consensus amino acid sequence $X_1X_2X_3X_4X_5$, wherein $X_1$ and $X_5$ comprise polar amino acids. In another embodiment, the peptides have a consensus amino acid sequence $X_1X_2X_3X_4X_5$, wherein $X_2$ and $X_4$ are asparagine (N) residues and $X_3$ is tryptophan (W). Compositions comprising same are also disclosed and uses thereof.

4 Claims, 21 Drawing Sheets

ANTI-BACTERIAL PEPTIDES AND METHODS OF TREATING DISEASES USING SAME

RELATED APPLICATIONS

This Application is a National Phase of PCT Patent Application No. PCT/IL2008/000039 having International filing date of Jan. 8, 2008, which claims the benefit of U.S. Provisional Application No. 60/879,343 filed on Jan. 9, 2007. The contents of the above Applications are all incorporated herein by reference.

FIELD AND BACKGROUND OF THE INVENTION

The present invention, in some embodiments thereof, relates to peptide agents comprising anti-bacterial properties and to methods of treating diseases using same.

Antibiotics, compounds with selective toxicity against infectious microorganisms, present humanity with enormous benefits and are credited with saving many millions of lives since their introduction in the 20th century. Bacterial antibiotic resistance however, has become one of the most important threats to modern health care. Infections caused by resistant bacteria frequently result in longer hospital stays, higher mortality and increased cost of treatment. Today there is a continuing need for new antibiotics to assist in the management of multiply resistant pathogens (e.g. multiply resistant *Staphyloccus* aureus or vancomycin-resistant *enterococcus*) and for methods of sensitizing antibiotic-resistant bacteria to antibiotics.

Over the last few years, a great deal of attention has been focused on toxin-antitoxin modules that are found on the chromosomes of many bacteria including pathogens, including *E. coli*. Each of these modules consists of a pair of genes, of which generally the downstream gene encodes for a stable toxin and the upstream gene encodes for a labile antitoxin. In *E. coli* alone, six toxin-antitoxin systems have been described. Among these, the most studied is mazEF, which was the first to be described as regulatable and responsible for bacterial programmed cell death [Aizenman, 1996, Proc. Natl. Acad. Sci. USA, 93, 6059-6063; Engelberg Kulka et al., 2006, PLoS Genetics 2, 1518-1526]. *E. coli* mazF specifies for the stable toxin MazF, and mazE specifies for the labile antitoxin, MazE. In vivo, MazE is degraded by the ATP-dependent ClpAP serine protease (but not by the proteases ClpXP or Lon). MazF is a sequence-specific endoribonuclease that preferentially cleaves single-stranded mRNAs at ACA sequences. MazE counteracts the action of MazF. Since MazE is a labile protein, preventing MazF-mediated action requires the continuous production of MazE. Thus, any stressful condition that prevents the expression of the chromosomally borne mazEF module will lead to the reduction of MazE in the cell, permitting toxin MazF to act freely. Such conditions include: (i) Briefly inhibiting transcription and/or translation by antibiotics like rifampicin, chloramphenicol and spectinomycin; (ii) Over-production of ppGpp that inhibits mazEF transcription; and iii) DNA damage caused by thymine starvation as well as by DNA damaging agents like mitomycin C, or nalidixic acid. These antibiotics and stressful conditions that are well known for causing bacterial cell death have been found to act through the mazEF module [Hazan et al., 2004, J. Bacteriol. 186, 3663-3669; Sat B. et al., 2001, J. Bacteriol., 183, 2041-2045; Sat B. et al., 2003, J. Bacteriol. 185, 1803-1807].

Additional background art includes U.S. Pat. Appl. No. 20070259813, which teaches peptides with antibiotic-like properties and International patent application PCT No. WO 01/64738 which teaches peptides capable of reacting with aminoglycans and transporting molecules of interest in eukaryotic or prokaryotic cells.

SUMMARY OF THE INVENTION

According to an aspect of some embodiments of the present invention there is provided an isolated peptide having no more than seven amino acids, comprising a consensus amino acid sequence $X_1X_2X_3X_4X_5$, wherein $X_1$ and $X_5$ comprise polar amino acids, the peptide having anti-bacterial activity.

According to an aspect of some embodiments of the present invention there is provided an isolated polynucleotide comprising a nucleic acid sequence encoding a polypeptide having no more than seven amino acids and comprising a consensus amino acid sequence $X_1X_2X_3X_4X_5$, wherein $X_1$ and $X_5$ comprise polar amino acids, the peptide having anti-bacterial activity.

According to an aspect of some embodiments of the present invention there is provided an anti-bacterial composition, comprising a carrier and as an active ingredient an isolated peptide having no more than seven amino acids, comprising an amino acid consensus sequence $X_1X_2X_3X_4X_5$, wherein $X_1$ and $X_5$ comprise polar amino acids.

According to an aspect of some embodiments of the present invention there is provided a method of treating a bacterial infection, the method comprising administering into a subject in need thereof a therapeutically effective amount of the isolated peptide having no more than seven amino acids, comprising a consensus amino acid sequence $X_1X_2X_3X_4X_5$, wherein $X_1$ and $X_5$ comprise polar amino acids, the peptide having anti-bacterial activity, thereby treating the bacterial infection.

According to an aspect of some embodiments of the present invention there is provided a solid support coated with the isolated peptide having no more than seven amino acids, comprising a consensus amino acid sequence $X_1X_2X_3X_4X_5$, wherein $X_1$ and $X_5$ comprise polar amino acids, the peptide having anti-bacterial activity.

According to an aspect of some embodiments of the present invention there is provided a method of killing bacteria, the method comprising contacting the bacteria with the isolated peptide having no more than seven amino acids, comprising a consensus amino acid sequence $X_1X_2X_3X_4X_5$, wherein $X_1$ and $X_5$ comprise polar amino acids, the peptide having anti-bacterial activity, thereby killing bacteria.

According to some embodiments of the invention, the polar amino acids are acidic amino acids.

According to some embodiments of the invention, the acidic amino acids comprise an amide derivative.

According to some embodiments of the invention, the at least one of X1 and X5 comprises an asparagine (N) residue.

According to some embodiments of the invention, the at least one of X1 and X5 comprises a glutamine (Q) residue.

According to some embodiments of the invention, the anti-bacterial activity comprises up-regulating MazF-mediated anti-bacterial activity.

According to some embodiments of the invention, the peptide is a pentapeptide.

According to some embodiments of the invention, the $X_3$ comprises a tryptophan (W) residue.

According to some embodiments of the invention, the $X_2$ and $X_4$ comprise asparagine residues.

According to some embodiments of the invention, the peptide has an amino acid sequence as set forth in SEQ ID NO: 1.

According to some embodiments of the invention, the peptide is attached to a sustained-release enhancing agent.

According to some embodiments of the invention, the sustained-release enhancing agent is selected from the group consisting of hyaluronic acid (HA), alginic acid (AA), polyhydroxyethyl methacrylate (Poly-HEMA), polyethylene glycol (PEG), glyme and polyisopropylacrylamide.

According to some embodiments of the invention, the isolated peptide is capable of up-regulating MazF-mediated anti-bacterial activity.

According to some embodiments of the invention, the anti-bacterial composition further comprises at least one agent capable of reducing a level of MazE.

According to some embodiments of the invention, the at least one agent comprises an antibiotic.

According to some embodiments of the invention, the antibiotic is selected from the group consisting of rifampicin, chloramphenicol and spectinomycin.

According to some embodiments of the invention, the at least one agent comprises a DNA damaging agent.

According to some embodiments of the invention, the DNA damaging agent is selected from the group consisting of mitomycin C., nalidixic acid and trimethoprim. According to some embodiments of the invention, the at least one agent comprises a serine analogue.

According to some embodiments of the invention, a formulation of the composition is selected from the group consisting of a spray, a cream, a mouthwash, a wipe, a foam, a soap, an oil, a solution, a lotion, an ointment, a paste and a gel.

According to some embodiments of the invention, the carrier is a pharmaceutically acceptable carrier.

According to some embodiments of the invention, the contacting is effected in vivo.

According to some embodiments of the invention, the contacting is effected ex vivo.

According to an aspect of some embodiments of the present invention there is provided an isolated peptide having no more than seven amino acids, comprising a consensus amino acid sequence $X_1X_2X_3X_4X_5$, wherein $X_2$ and $X_4$ are asparagine (N) residues, $X_3$ is tryptophan (W), the peptide being capable of reducing MazF-mediated anti-bacterial activity.

According to an aspect of some embodiments of the present invention there is provided a pharmaceutical composition, comprising a pharmaceutically acceptable carrier and as an active agent the isolated peptide having no more than seven amino acids, comprising a consensus amino acid sequence $X_1X_2X_3X_4X_5$, wherein $X_2$ and $X_4$ are asparagine (N) residues, $X_3$ is tryptophan (W), the peptide being capable of reducing MazF-mediated anti-bacterial activity.

According to an aspect of some embodiments of the present invention there is provided a method of sensitizing antibiotic-resistant bacterial cells to an antibiotic, the antibiotic-resistant bacterial cells comprising a MazEF system, the method comprising contacting the bacterial cells with an agent capable of reducing the activity of MazF, thereby sensitizing the antibiotic resistant bacterial cells to the antibiotic.

According to an aspect of some embodiments of the present invention there is provided a method of killing an antibiotic-resistant bacterial cell, the antibiotic-resistant bacterial cell comprising a MazEF system, the method comprising (a) contacting the cell with an agent capable of reducing the activity of MazF to sensitize the antibiotic-resistant bacterial cell to the antibiotic; and subsequently (b) contacting the sensitized antibiotic-resistant bacterial cell with an antibiotic, thereby killing the antibiotic resistant bacterial cell.

According to an aspect of some embodiments of the present invention there is provided a kit comprising the isolated peptide having no more than seven amino acids, comprising a consensus amino acid sequence $X_1X_2X_3X_4X_5$, wherein $X_2$ and $X_4$ are asparagine (N) residues, $X_3$ is tryptophan (W), the peptide being capable of reducing MazF-mediated anti-bacterial activity, and an antibiotic.

According to some embodiments of the invention, the peptide has an amino acid sequence as set forth in SEQ ID NOs: 2 and 6.

According to some embodiments of the invention, the pharmaceutical composition further comprises an antibiotic.

According to some embodiments of the invention, the antibiotic-resistant bacterial cells comprise vancomycin-resistant bacterial cells.

According to some embodiments of the invention, the bacterial cells comprise enterococci cells.

According to some embodiments of the invention, the agent capable of reducing the activity of MazF comprises a peptide capable of abrogating a toxic activity of MazF.

According to some embodiments of the invention, the peptide is the isolated peptide having no more than seven amino acids, comprising a consensus amino acid sequence $X_1X_2X_3X_4X_5$, wherein $X_2$ and $X_4$ are asparagine (N) residues, $X_3$ is tryptophan (W), the peptide being capable of reducing MazF-mediated anti-bacterial activity.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings and images. With specific reference now to the drawings and images in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 14A illustrates that each of the five amino acids is important for EDF activity. The five peptides analyzed include NNWNN (SEQ ID NO: 1); GNWNN (SEQ ID NO: 2); NGWNN (SEQ ID NO: 3); NNGNN (SEQ ID NO: 4); NNWGN (SEQ ID NO: 5); and NNWNG (SEQ ID NO: 6). The importance of size and external Asn residues for EDF activity is illustrated in FIG. 14B. Chemically synthesized EDF (SEQ ID NO: 1) or its modified derivatives were added at various concentrations to diluted cultures of E. Coli MC41relA$^+$. No EDF was added to a control culture. The modified derivatives that were added include NWN (SEQ ID NO: 7); NNNWNNN (SEQ ID NO: 8); QNWNN (SEQ ID NO: 9); NNWNQ (SEQ ID NO: 10); and GNWNG (SEQ ID NO: 11). Samples were incubated with rifampicin as described in Example 1.

DESCRIPTION OF SPECIFIC EMBODIMENTS OF THE INVENTION

The present invention, in some embodiments thereof, relates to peptide agents comprising anti-bacterial properties and to methods of treating diseases using same.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Various toxin-antitoxin modules exist on the chromosomes of many bacteria including E. coli. Each of these modules consists of a pair of genes, of which generally the downstream gene encodes for a stable toxin and the upstream gene encodes for a labile antitoxin. In E. coli alone, six toxin-antitoxin systems have been described.

Figure 1:
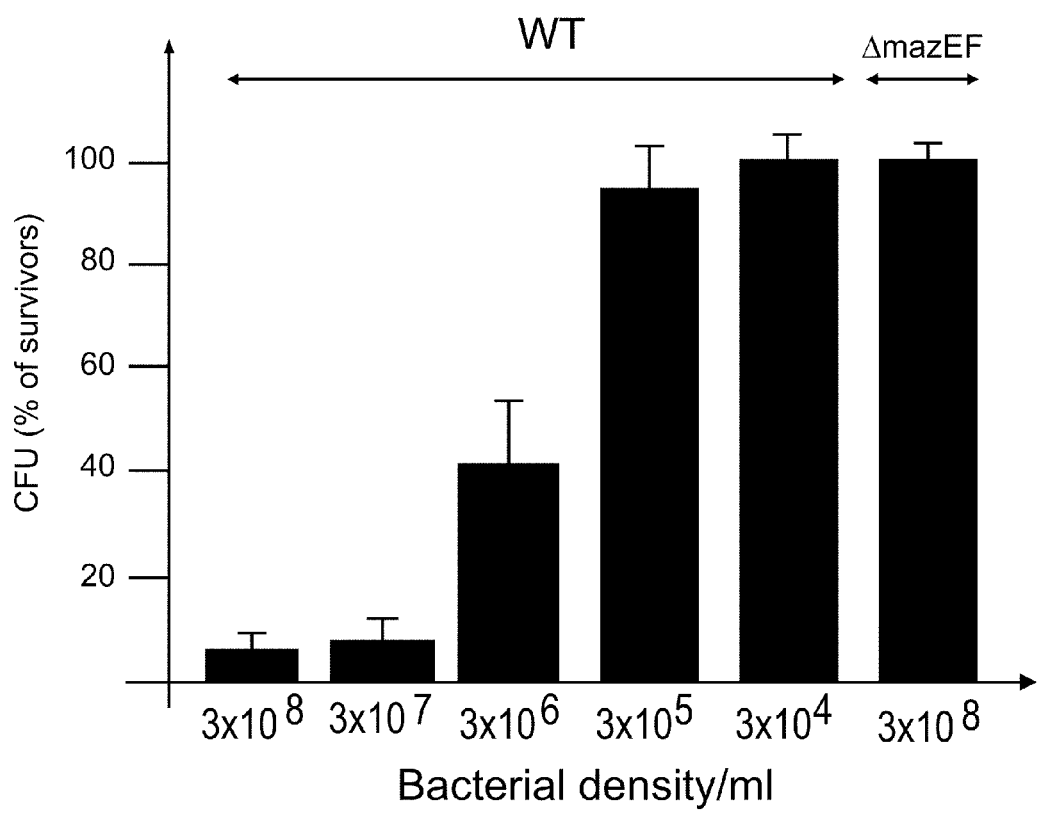
FIG. 1 is a bar graph illustrating that mazEF-mediated cell death is dependent on cell density. The percentage of surviving CFUs is represented by the ratio of "treated cells"/"untreated cells". Bars in this and the following figures indicate standard deviations.
Figure 2A:
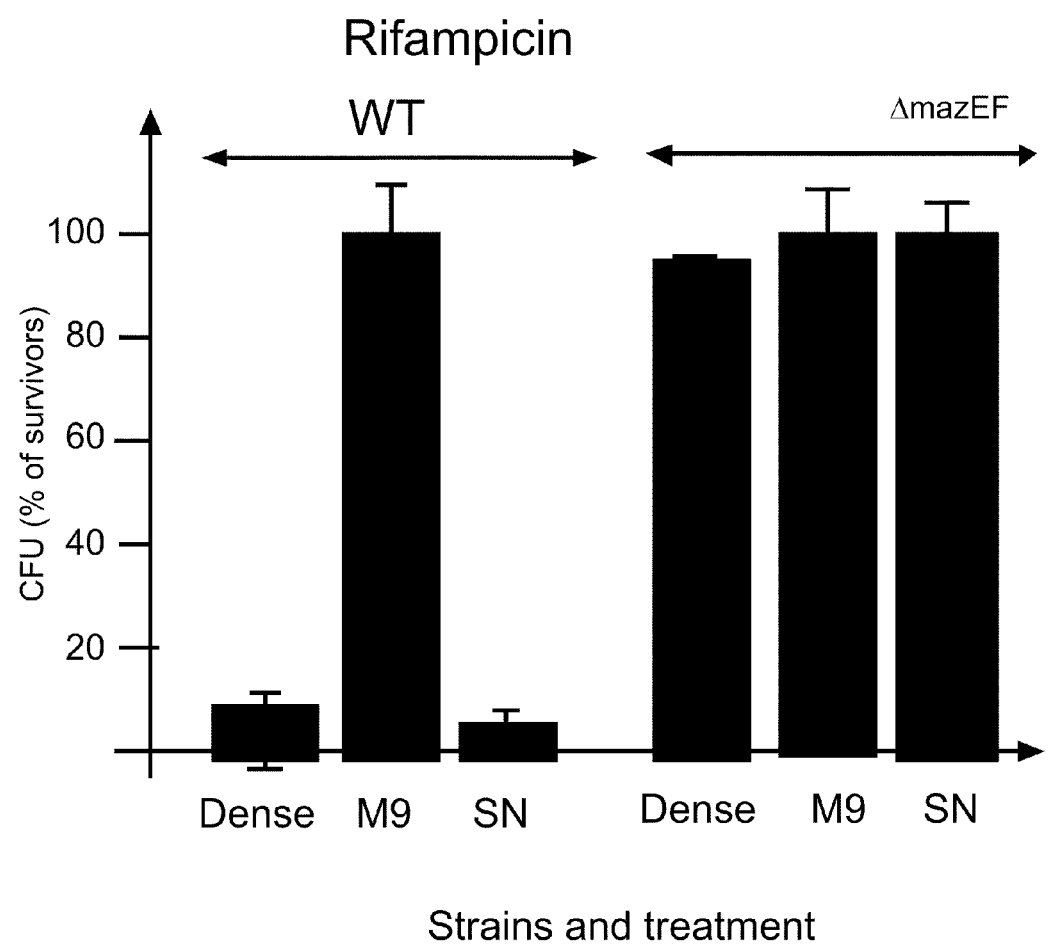
FIGS. 2A-C are bar graphs illustrating that the supernatant of a dense culture can restore mazEF-mediated cell death induced by various stressful conditions.
Figure 2B:
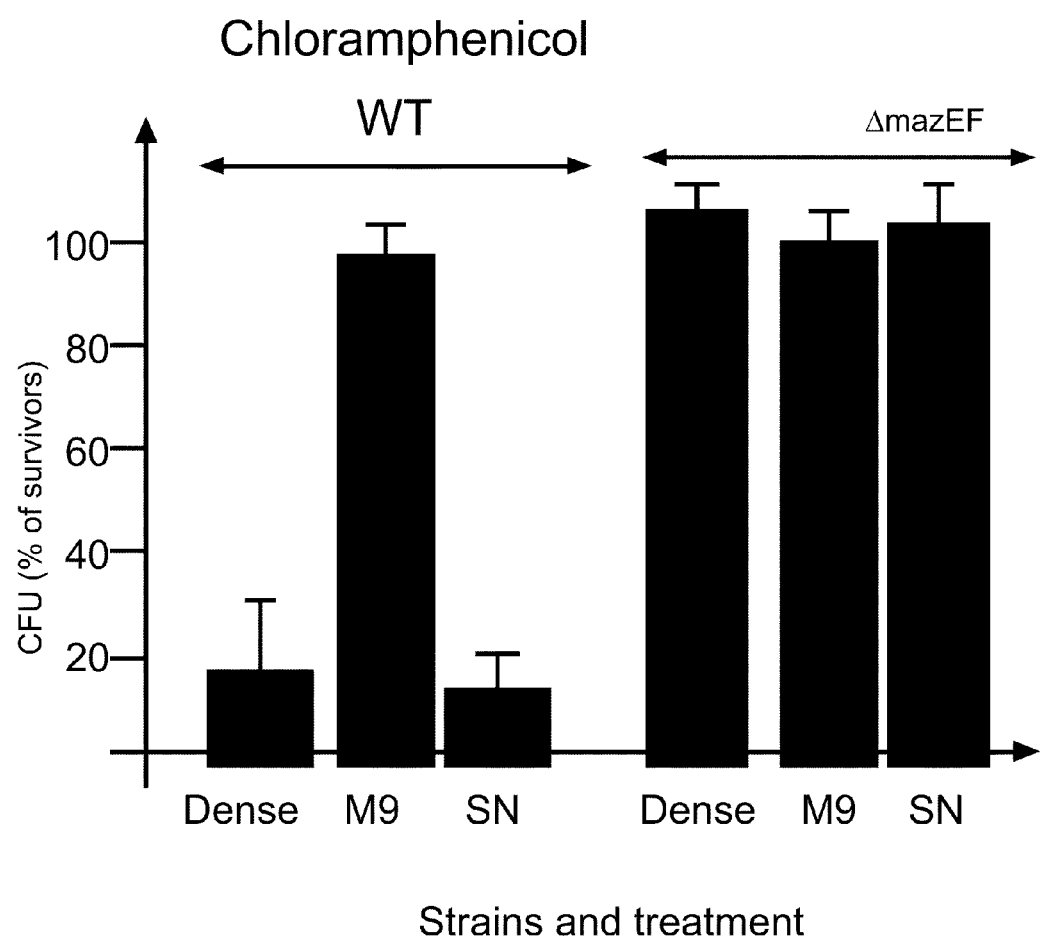
Figure 2C:
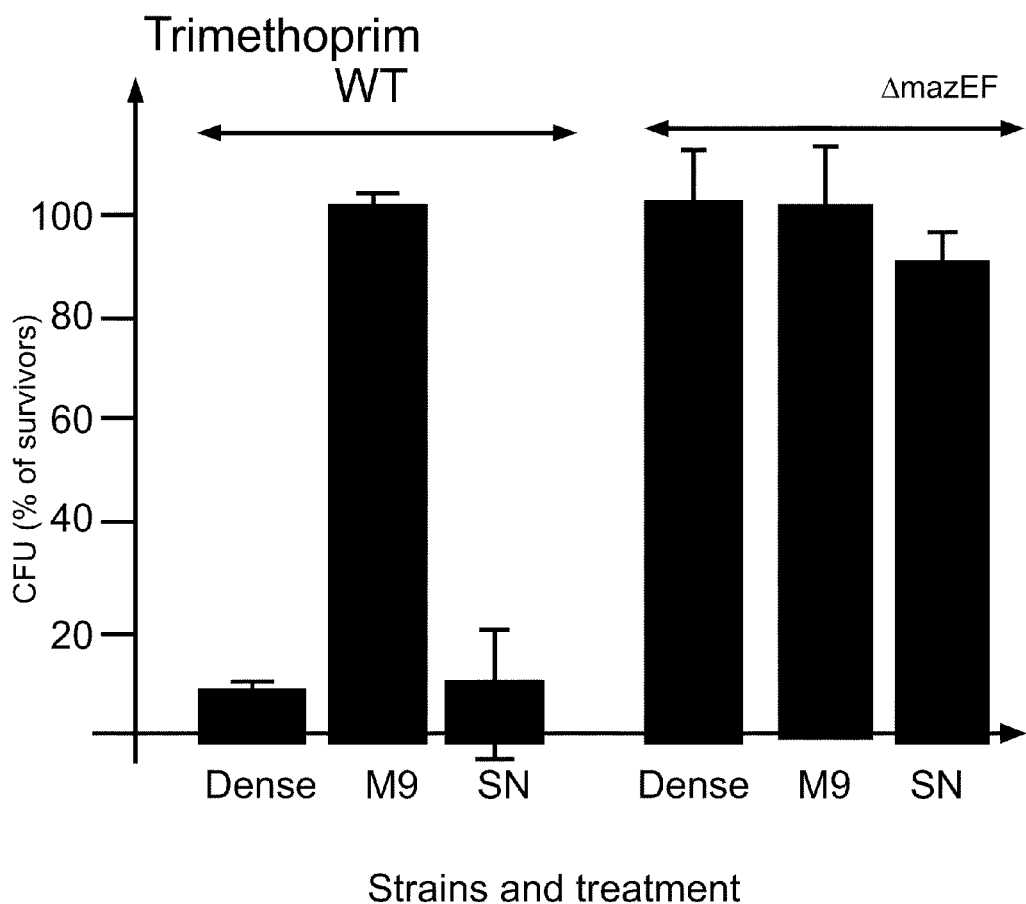

Whilst studying characteristics of cell death caused by one of these toxin-antitoxin modules, (mazEF), the present inventors noticed that death occurs in a dense culture ($10^7$-$10^8$ cells/ml), while not in a diluted culture ($10^4$-$10^5$ cells/ml) (FIG. 1). Following corroboration of the fact that a supernatant of a dense culture is capable of restoring mazEF-mediated cell death of a diluted culture (FIGS. 3A-B), the present inventors deduced that mazEF-mediated cell death requires an extracellular factor. This factor, also referred to herein as the Extra-cellular Death Factor (EDF) was shown to be required when mazEF-mediated cell death was triggered by all studied stressful conditions. Among them, the inhibitor of transcription rifampicin (FIG. 2A), the inhibitor of translational chloramphenicol (FIG. 2B), and the DNA damaging agent trimethoprim (FIG. 2C).

Not only did EDF permit the activation of MazF (FIGS. 2A-C), but EDF action was shown to be dependent on the presence of the mazEF module in the recipient cells (FIG. 5) and reciprocally MazF activation led to an increase in the production of EDF (FIG. 4), resulting in an increase in cell death.

Figure 9A:
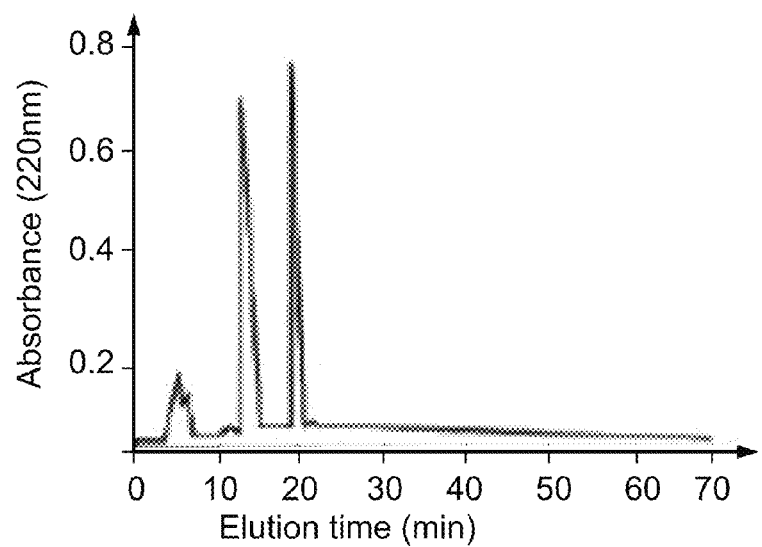
FIGS. 9A-B are graphs depicting the results of HPLC analysis of the EDF peptide.
Figure 9B:
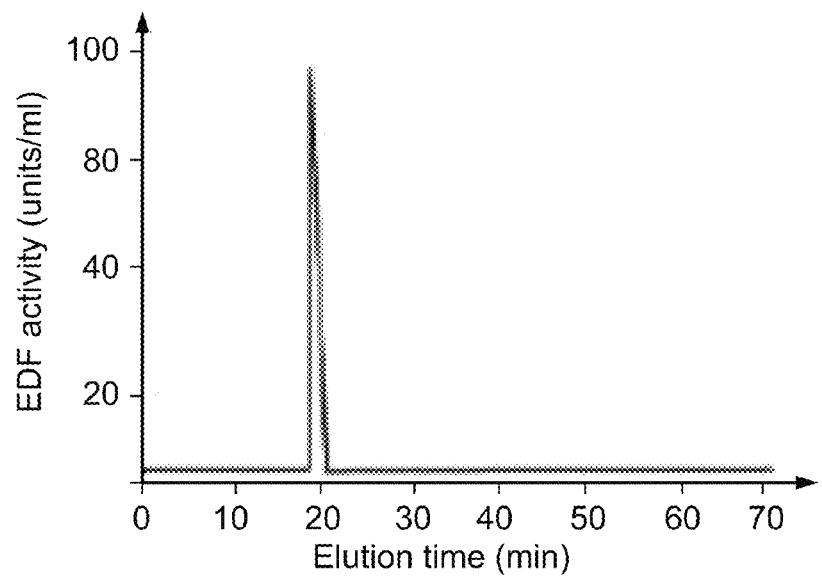
Figure 10A:
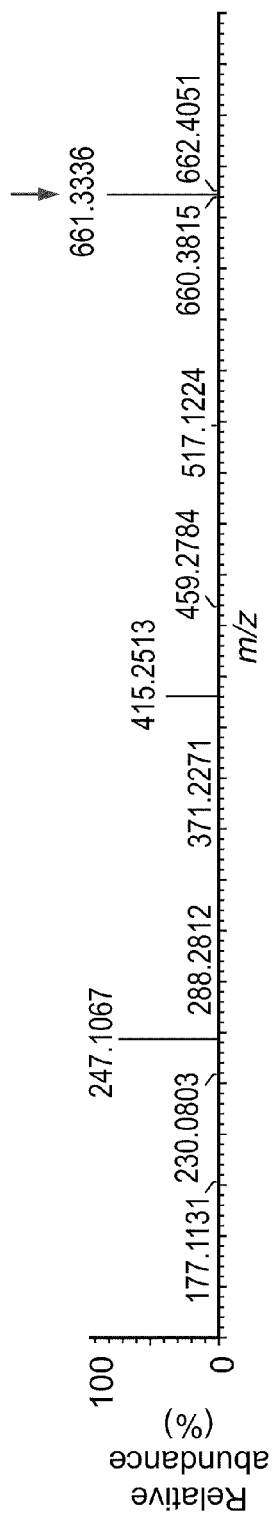
FIG. 10A illustrates the results obtained by electrospray ionization mass spectroscopy (ESI-MS) following purification of EDF as described herein. Peaks range from 200 to 662 MW, among them one at 661 MW is marked by an arrow.

Whilst further reducing the present invention to practice, the present inventors isolated this factor using high performance liquid chromatography (HPLC; FIGS. 9A-B and FIG. 11) and electrospray ionization mass spectroscopy (ESI MS; FIG. 10A). Fragmentation (MS/MS) analysis of material comprising the factor (FIG. 10B) revealed that EDF is a linear peptide as determined by nuclear magnetic resonance (NMR) analysis (FIG. 10C) with the amino acid sequence Asn-Asn-Trp-Asn-Asn (NNWNN).

The present inventors showed that the isolated peptide was capable of killing E. coli cells both alone (FIG. 7) and in combination with other antibiotics (FIG. 8, FIGS. 12A-C and FIGS. 13A-B).

Figure 15:
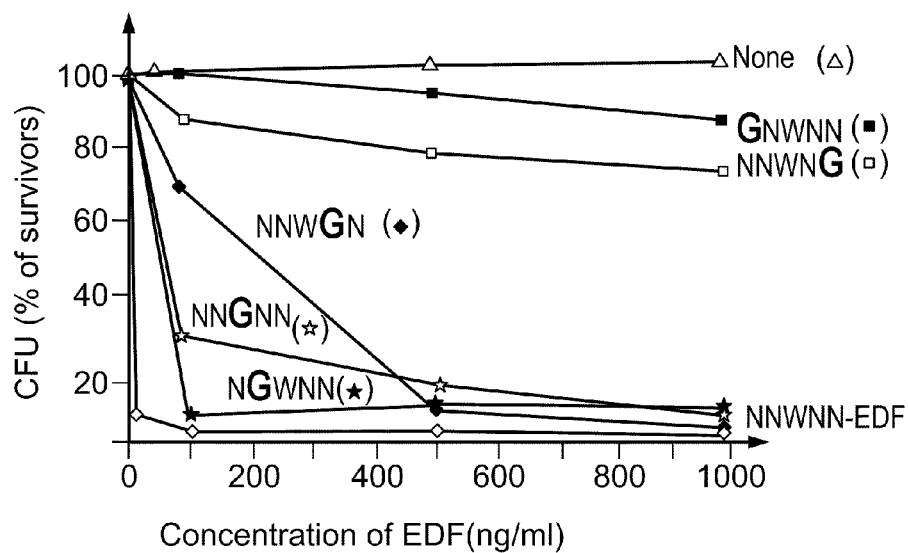
FIG. 15 is a graph illustrating the ability of mutant EDF molecules to inhibit wild type EDF activity. The five peptides analyzed include NNWNN (SEQ ID NO: 1); GNWNN (SEQ ID NO: 2); NGWNN (SEQ ID NO: 3); NNGNN (SEQ ID NO: 4); NNWGN (SEQ ID NO: 5); and NNWNG (SEQ ID NO: 6).

Structure activity analyses revealed that substitution of the first and last amino acid of EDF generated peptides capable of blocking the activity of this pentapeptide (FIG. 15).

Thus according to one aspect of the present invention there is provided an isolated peptide having no more than seven amino acids, comprising a consensus amino acid sequence $X_1X_2X_3X_4X_5$, wherein $X_1$ and $X_5$ comprise polar amino acids, the peptide having anti-bacterial activity.

As used herein, the phrase "anti-bacterial activity" refers to either bactericidal or bacteriostatic activity, or both. According to one embodiment the anti-bacterial activity comprises up-regulating MazF-mediated anti-bacterial activity.

MazF is the toxin component of the mazEF toxin-antitoxin module located on many bacterial chromosomes, including those of pathogens. MazF encodes a stable toxin, which is a sequence-specific endoribonuclease that preferentially cleaves single-stranded mRNAs at ACA sequences. Exemplary bacteria known to comprise the mazEF toxin-antitoxin module include: (i) The main invasive enteric pathogens as the enteroinvasive Escherichia coli (E. coli) (EIEC) causing diarrhoea, Enterohemorragic E. coli (EHEC) causing hemorrhagic colitis., and *E. coli* (EIEC) and *Shigella* causing dysentery; (ii) The uripathogenic *E. coli* (UPEC) causing urinary tract infection; (iii) *Staphylicoccus aureus* causing pyogenic infections and abscesses of many organs, septicemia, toxic shock, pneumonia, meningitis, endocarditis and food poisoning; (iv) *Pseodomonas aeruginosa* causing pyogenic infection in burn patients, and lung infection in cystic fibrosis; (v) *Mycobacterium tuberculosis* which is one of the most devastating pathogen where one third of the world population is infected and eight million people develop active tuberculosis each year; (vi) The spore forming bacteria *Bacillus anthrax* causing cutaneous, inhalation and gastrointestinal anthrax disease, and used in bio-terrorism; (vii) *enterococci*.

As mentioned herein above, the peptides of the present invention comprise polar amino acids at positions X1 and X5.

The phrase "polar amino acids" refers to both naturally occurring and synthetic polar amino acids. Typically polar amino acids comprise side-chains that prefer to reside in an aqueous (i.e. water) environment. Exemplary natural polar amino acids include, but are not limited to arginine, lysine, aspartate, glutamate, asparagine and glutamine. According to one embodiment, the polar amino acids are acidic amino acids.

As used herein, the phrase "acidic amino acid" refers to a polar amino acid which is negatively charged at physiological pH. Exemplary acidic amino acids and their amide derivatives include aspartic acid (amide derivative=asparagine) and glutamic acid (amide derivative=glutamine)

According to one embodiment, the peptide comprises an amino acid sequence as set forth in SEQ ID NO: 1, or a derivative thereof. The derivative may include several types of derivation (replacements and deletions, chemical modification and/or change in peptidic backbone) as further described herein below.

According to another embodiment at least one of X1 and X5 comprises an asparagine (N) residue.

According to yet another embodiment at least one of X1 and X5 comprises a glutamine (Q) residue.

According to still another embodiment both X1 and X5 comprise an asparagine or glutamine residue.

According to still another embodiment, $X_3$ comprises a tryptophan (W) residue. According to still another embodiment, $X_2$ and $X_4$ comprise asparagine residues.

It will be appreciated that although the peptides of the present invention are restricted by the fact that both X1 and X5 comprise polar amino acids, amino acids at positions X2-X4 may be different from those set forth in SEQ ID NO: 1. The replacement may be by naturally occurring amino acids, (both conservative and non-conservative substitutions), by non-naturally occurring amino acids (both conservative and non-conservative substitutions), or with organic moieties which serve either as true peptidomimetics (i.e. having the same steric and electrochemical properties as the replaced amino acid), or merely serve as spacers in lieu of an amino acid, so as to keep the spatial relations between the amino acid spanning this replaced amino acid. Guidelines for the determination of the replacements and substitutions are given herein below.

The present inventors have revealed that substitution of at least one of the polar amino acids of X1 and X5 of the peptide of SEQ ID NO: 1 with a non-polar amino acid (e.g. glycine) confers antagonistic properties to the peptide. Thus, for example, the present inventors have shown that peptides of SEQ ID NOs: 2 and 6 are capable of antagonizing the anti-bacterial property of the peptide of SEQ ID NO: 1. Thus according to another aspect of the present invention there is provided an isolated peptide being no more than ten amino acids, comprising a consensus amino acid sequence $X_1X_2X_3X_4X_5$, wherein $X_2$ and $X_4$ are asparagine (N) residues, $X_3$ is tryptophan (W), the peptide being capable of reducing MazF-mediated anti-bacterial activity. Uses of such peptides are described herein below.

According to one embodiment, the peptides of the present invention are pentapeptides. However, the present invention also contemplates adding to the peptides of the present invention additional amino acids up to a maximum number of seven. These additional amino acids may be added to improve physiological properties of the peptide or to modulate the activity of the peptides.

The term "peptide" as used herein refers to a polymer of natural or synthetic amino acids, encompassing native peptides (either degradation products, synthetically synthesized polypeptides or recombinant polypeptides) and peptidomimetics (typically, synthetically synthesized peptides), as well as peptoids and semipeptoids which are polypeptide analogs, which may have, for example, modifications rendering the peptides even more stable while in a body or more capable of penetrating into cells.

Such modifications include, but are not limited to N terminus modification, C terminus modification, polypeptide bond modification, including, but not limited to, CH2-NH, CH2-S, CH2-S=O, O=C—NH, CH2-O, CH2-CH2, S=C—NH, CH=CH or CF=CH, backbone modifications, and residue modification. Methods for preparing peptidomimetic compounds are well known in the art and are specified, for example, in Quantitative Drug Design, C.A. Ramsden Gd., Chapter 17.2, F. Choplin Pergamon Press (1992), which is incorporated by reference as if fully set forth herein. Further details in this respect are provided hereinunder.

Polypeptide bonds (—CO—NH—) within the polypeptide may be substituted, for example, by N-methylated bonds (—N(CH3)-CO—), ester bonds (—C(R)H—C—O—O—C(R)—N—), ketomethylen bonds (—CO—CH2-), α-aza bonds (—NH—N(R)—CO—), wherein R is any alkyl, e.g., methyl, carba bonds (—CH2-NH—), hydroxyethylene bonds (—CH(OH)—CH2-), thioamide bonds (—CS—NH—), olefinic double bonds (—CH=CH—), retro amide bonds (—NH—CO—), polypeptide derivatives (—N(R)—CH2-CO—), wherein R is the "normal" side chain, naturally presented on the carbon atom.

These modifications can occur at any of the bonds along the polypeptide chain and even at several (2-3) at the same time.

Natural aromatic amino acids, Trp, Tyr and Phe, may be substituted for synthetic non-natural acid such as Phenylglycine, TIC, naphthylelanine (Nol), ring-methylated derivatives of Phe, halogenated derivatives of Phe or o-methyl-Tyr.

In addition to the above, the polypeptides of the present invention may also include one or more modified amino acids or one or more non-amino acid monomers (e.g. fatty acids, complex carbohydrates etc).

As used herein in the specification and in the claims section below the term "amino acid" or "amino acids" is understood to include the 20 naturally occurring amino acids; those amino acids often modified post-translationally in vivo, including, for example, hydroxyproline, phosphoserine and phosphothreonine; and other unusual amino acids including, but not limited to, 2-aminoadipic acid, hydroxylysine, isodesmosine, nor-valine, nor-leucine and ornithine. Furthermore, the term "amino acid" includes both D- and L-amino acids (stereoisomers).

Tables 1 and 2 below list naturally occurring amino acids (Table 1) and non-conventional or modified amino acids (Table 2) which can be used with the present invention.

TABLE 1

| Amino Acid | Three-Letter Abbreviation | One-letter Symbol |
|---|---|---|
| alanine | Ala | A |
| Arginine | Arg | R |
| Asparagine | Asn | N |
| Aspartic acid | Asp | D |
| Cysteine | Cys | C |
| Glutamine | Gln | Q |
| Glutamic Acid | Glu | E |
| glycine | Gly | G |
| Histidine | His | H |
| isoleucine | Iie | I |
| leucine | Leu | L |
| Lysine | Lys | K |
| Methionine | Met | M |
| phenylalanine | Phe | F |
| Proline | Pro | P |
| Serine | Ser | S |
| Threonine | Thr | T |
| tryptophan | Trp | W |
| tyrosine | Tyr | Y |
| Valine | Val | V |
| Any amino acid as above | Xaa | X |

TABLE 2

| Non-conventional amino acid | Code |
|---|---|
| α-aminobutyric acid | Abu |
| α-amino-α-methylbutyrate | Mgabu |
| aminocyclopropane-carboxylate | Cpro |
| aminoisobutyric acid | Aib |
| aminonorbornyl-carboxylate | Norb |
| cyclohexylalanine | Chexa |
| cyclopentylalanine | Cpen |
| D-alanine | Dal |
| D-arginine | Darg |
| D-aspartic acid | Dasp |
| D-cysteine | Dcys |
| D-glutamine | Dgln |
| D-glutamic acid | Dglu |
| D-histidine | Dhis |
| D-isoleucine | Dile |
| D-leucine | Dleu |
| D-lysine | Dlys |
| D-methionine | Dmet |
| D-ornithine | Dorn |
| D-phenylalanine | Dphe |
| D-proline | Dpro |
| D-serine | Dser |
| D-threonine | Dthr |
| D-tryptophan | Dtrp |
| D-tyrosine | Dtyr |
| D-valine | Dval |
| D-α-methylalanine | Dmala |
| D-α-methylarginine | Dmarg |
| D-α-methylasparagine | Dmasn |
| D-α-methylaspartate | Dmasp |
| D-α-methylcysteine | Dmcys |
| D-α-methylglutamine | Dmgln |
| D-α-methylhistidine | Dmhis |
| D-α-methylisoleucine | Dmile |
| D-α-methylleucine | Dmleu |
| D-α-methyllysine | Dmlys |
| D-α-methylmethionine | Dmmet |
| D-α-methylornithine | Dmorn |
| D-α-methylphenylalanine | Dmphe |
| D-α-methylproline | Dmpro |
| D-α-methylserine | Dmser |
| D-α-methylthreonine | Dmthr |
| D-α-methyltryptophan | Dmtrp |
| D-α-methyltyrosine | Dmty |
| D-α-methylvaline | Dmval |
| D-α-methylalnine | Dnmala |
| D-α-methylarginine | Dnmarg |
| D-α-methylasparagine | Dnmasn |

TABLE 2-continued

| Non-conventional amino acid | Code |
|---|---|
| D-α-methylasparatate | Dnmasp |
| D-α-methylcysteine | Dnmcys |
| D-N-methylleucine | Dnmleu |
| D-N-methyllysine | Dnmlys |
| N-methylcyclohexylalanine | Nmchexa |
| D-N-methylornithine | Dnmorn |
| N-methylglycine | Nala |
| N-methylaminoisobutyrate | Nmaib |
| N-(1-methylpropyl)glycine | Nile |
| N-(2-methylpropyl)glycine | Nile |
| N-(2-methylpropyl)glycine | Nleu |
| D-N-methyltryptophan | Dnmtrp |
| D-N-methyltyrosine | Dnmtyr |
| D-N-methylvaline | Dnmval |
| γ-aminobutyric acid | Gabu |
| L-t-butylglycine | Tbug |
| L-ethylglycine | Etg |
| L-homophenylalanine | Hphe |
| L-α-methylarginine | Marg |
| L-α-methylaspartate | Masp |
| L-α-methylcysteine | Mcys |
| L-α thylglutamine | Mgln |
| L-α-methylhistidine | Mhis |
| L-α-methylisoleucine | Mile |
| D-N-methylglutamine | Dnmgln |
| D-N-methylglutamate | Dnmglu |
| D-N-methylhistidine | Dnmhis |
| D-N-methylisoleucine | Dnmile |
| D-N-methylleucine | Dnmleu |
| D-N-methyllysine | Dnmlys |
| N-methylcyclohexylalanine | Nmchexa |
| D-N-methylornithine | Dnmorn |
| N-methylglycine | Nala |
| N-methylaminoisobutyrate | Nmaib |
| N-(1-methylpropyl)glycine | Nile |
| N-(2-methylpropyl)glycine | Nleu |
| D-N-methyltryptophan | Dnmtrp |
| D-N-methyltyrosine | Dnmtyr |
| D-N-methylvaline | Dnmval |
| γ-aminobutyric acid | Gabu |
| L-t-butylglycine | Tbug |
| L-ethylglycine | Etg |
| L-homophenylalanine | Hphe |
| L-α-methylarginine | Marg |
| L-α-methylaspartate | Masp |
| L-α-methylcysteine | Mcys |
| L-α-methylglutamine | Mgln |
| L-α ethylhistidine | Mhis |
| L-α thylisoleucine | Mile |
| L-α-methylleucine | Mleu |
| L-α-methylmethionine | Mmet |
| L-α-methylnorvaline | Mnva |
| L-α-methylphenylalanine | Mphe |
| L-α-methylserine | mser |
| L-α ethylvaline | Mtrp |
| L-α-methylleucine | Mvalnbhm |
| N-(N-(2,2-diphenylethyl) carbamylmethyl-glycine | Nnbhm |
| 1-carboxy-1-(2,2-diphenyl hylamino)cyclopropane | Nmbc |
| L-N-methylalanine | Nmala |
| L-N-methylarginine | Nmarg |
| L-N-methylasparagine | Nmasn |
| L-N-methylaspartic acid | Nmasp |
| L-N-methylcysteine | Nmcys |
| L-N-methylglutamine | Nmgin |
| L-N-methylglutamic acid | Nmglu |
| L-N-methylhistidine | Nmhis |
| L-N-methylisolleucine | Nmile |
| L-N-methylleucine | Nmleu |
| L-N-methyllysine | Nmlys |
| L-N-methylmethionine | Nmmet |
| L-N-methylnorleucine | Nmnle |
| L-N-methylnorvaline | Nmnva |
| L-N-methylornithine | Nmorn |
| L-N-methylphenylalanine | Nmphe |
| L-N-methylproline | Nmpro |
| L-N-methylserine | Nmser |

TABLE 2-continued

| Non-conventional amino acid | Code |
| --- | --- |
| L-N-methylthreonine | Nmthr |
| L-N-methyltryptophan | Nmtrp |
| L-N-methyltyrosine | Nmtyr |
| L-N-methylvaline | Nmval |
| L-N-methylethylglycine | Nmetg |
| L-N-methyl-t-butylglycine | Nmtbug |
| L-norleucine | Nle |
| L-norvaline | Nva |
| α-methyl-aminoisobutyrate | Maib |
| α-methyl-γ-aminobutyrate | Mgabu |
| α ethylcyclohexylalanine | Mchexa |
| α-methylcyclopentylalanine | Mcpen |
| α-methyl-α-napthylalanine | Manap |
| α-methylpenicillamine | Mpen |
| N-(4-aminobutyl)glycine | Nglu |
| N-(2-aminoethyl)glycine | Naeg |
| N-(3-aminopropyl)glycine | Norn |
| N-amino-α-methylbutyrate | Nmaabu |
| α-napthylalanine | Anap |
| N-benzylglycine | Nphe |
| N-(2-carbamylethyl)glycine | Ngln |
| N-(carbamylmethyl)glycine | Nasn |
| N-(2-carboxyethyl)glycine | Nglu |
| N-(carboxymethyl)glycine | Nasp |
| N-cyclobutylglycine | Ncbut |
| N-cycloheptylglycine | Nchep |
| N-cyclohexylglycine | Nchex |
| N-cyclodecylglycine | Ncdec |
| N-cyclododeclglycine | Ncdod |
| N-cyclooctylglycine | Ncoct |
| N-cyclopropylglycine | Ncpro |
| N-cycloundecylglycine | Ncund |
| N-(2,2-diphenylethyl)glycine | Nbhm |
| N-(3,3-diphenylpropyl)glycine | Nbhe |
| N-(3-indolylyethyl)glycine | Nhtrp |
| N-methyl-γ-aminobutyrate | Nmgabu |
| D-N-methylmethionine | Dnmmet |
| N-methylcyclopentylalanine | Nmcpen |
| D-N-methylphenylalanine | Dnmphe |
| D-N-methylproline | Dnmpro |
| D-N-methylserine | Dnmser |
| D-N-methylserine | Dnmser |
| D-N-methylthreonine | Dnmthr |
| N-(1-methylethyl)glycine | Nva |
| N-methyla-napthylalanine | Nmanap |
| N-methylpenicillamine | Nmpen |
| N-(p-hydroxyphenyl)glycine | Nhtyr |
| N-(thiomethyl)glycine | Ncys |
| penicillamine | Pen |
| L-α-methylalanine | Mala |
| L-α-methylasparagine | Masn |
| L-α-methyl-t-butylglycine | Mtbug |
| L-methylethylglycine | Metg |
| L-α-methylglutamate | Mglu |
| L-α-methylhomo phenylalanine | Mhphe |
| N-(2-methylthioethyl)glycine | Nmet |
| N-(3-guanidinopropyl)glycine | Narg |
| N-(1-hydroxyethyl)glycine | Nthr |
| N-(hydroxyethyl)glycine | Nser |
| N-(imidazolylethyl)glycine | Nhis |
| N-(3-indolylyethyl)glycine | Nhtrp |
| N-methyl-γ-aminobutyrate | Nmgabu |
| D-N-methylmethionine | Dnmmet |
| N-methylcyclopentylalanine | Nmcpen |
| D-N-methylphenylalanine | Dnmphe |
| D-N-methylproline | Dnmpro |
| D-N-methylserine | Dnmser |
| D-N-methylthreonine | Dnmthr |
| N-(1-methylethyl)glycine | Nval |
| N-methyla-napthylalanine | Nmanap |
| N-methylpenicillamine | Nmpen |
| N-(p-hydroxyphenyl)glycine | Nhtyr |
| N-(thiomethyl)glycine | Ncys |
| penicillamine | Pen |
| L-α-methylalanine | Mala |
| L-α-methylasparagine | Masn |
| L-α-methyl-t-butylglycine | Mtbug |
| L-methylethylglycine | Metg |
| L-α-methylglutamate | Mglu |
| L-α-methylhomophenylalanine | Mhphe |
| N-(2-methylthioethyl)glycine | Nmet |
| L-α-methyllysine | Mlys |
| L-α-methylnorleucine | Mnle |
| L-α-methylornithine | Morn |
| L-α-methylproline | Mpro |
| L-α-methylthreonine | Mthr |
| L-α-methyltyrosine | Mtyr |
| L-N-methylhomophenylalanine | Nmhphe |
| N-(N-(3,3-diphenylpropyl) carbamylmethyl(1)glycine | Nnbhe |

As mentioned herein above, the three amino acids in-between the two polar amino acids (i.e. X2, X3 and X4) may be substituted from those set forth in SEQ ID NO: 1, either conservatively or non-conservatively.

The term "conservative substitution" as used herein, refers to the replacement of an amino acid present in the native sequence in the peptide with a naturally or non-naturally occurring amino or a peptidomimetics having similar steric properties. Where the side-chain of the native amino acid to be replaced is either polar or hydrophobic, the conservative substitution should be with a naturally occurring amino acid, a non-naturally occurring amino acid or with a peptidomimetic moiety which is also polar or hydrophobic (in addition to having the same steric properties as the side-chain of the replaced amino acid).

As naturally occurring amino acids are typically grouped according to their properties, conservative substitutions by naturally occurring amino acids can be easily determined bearing in mind the fact that in accordance with the invention replacement of charged amino acids by sterically similar non-charged amino acids are considered as conservative substitutions.

For producing conservative substitutions by non-naturally occurring amino acids it is also possible to use amino acid analogs (synthetic amino acids) well known in the art. A peptidomimetic of the naturally occurring amino acid is well documented in the literature known to the skilled practitioner.

When affecting conservative substitutions the substituting amino acid should have the same or a similar functional group in the side chain as the original amino acid.

The phrase "non-conservative substitutions" as used herein refers to replacement of the amino acid as present in the parent sequence by another naturally or non-naturally occurring amino acid, having different electrochemical and/or steric properties. Thus, the side chain of the substituting amino acid can be significantly larger (or smaller) than the side chain of the native amino acid being substituted and/or can have functional groups with significantly different electronic properties than the amino acid being substituted. Examples of non-conservative substitutions of this type include the substitution of phenylalanine or cyclohexylmethyl glycine for alanine, isoleucine for glycine, or —NH—CH[(—CH$_2$)$_5$—COOH]—CO— for aspartic acid. Those non-conservative substitutions which fall under the scope of the present invention are those which still constitute a peptide having anti-bacterial properties.

As mentioned, the N and C termini of the peptides of the present invention may be protected by function groups. Suitable functional groups are described in Green and Wuts, "Protecting Groups in Organic Synthesis", John Wiley and Sons, Chapters 5 and 7, 1991, the teachings of which are incorporated herein by reference. Preferred protecting groups are those that facilitate transport of the compound attached thereto into a cell, for example, by reducing the hydrophilicity and increasing the lipophilicity of the compounds.

These moieties can be cleaved in vivo, either by hydrolysis or enzymatically, inside the cell. Hydroxyl protecting groups include esters, carbonates and carbamate protecting groups. Amine protecting groups include alkoxy and aryloxy carbonyl groups, as described above for N-terminal protecting groups. Carboxylic acid protecting groups include aliphatic, benzylic and aryl esters, as described above for C-terminal protecting groups. In one embodiment, the carboxylic acid group in the side chain of one or more glutamic acid or aspartic acid residue in a peptide of the present invention is protected, preferably with a methyl, ethyl, benzyl or substituted benzyl ester.

Examples of N-terminal protecting groups include acyl groups (—CO—R1) and alkoxy carbonyl or aryloxy carbonyl groups (—CO—O—R1), wherein R1 is an aliphatic, substituted aliphatic, benzyl, substituted benzyl, aromatic or a substituted aromatic group. Specific examples of acyl groups include acetyl, (ethyl)-CO—, n-propyl-CO—, iso-propyl-CO—, n-butyl-CO—, sec-butyl-CO—, t-butyl-CO—, hexyl, lauroyl, palmitoyl, myristoyl, stearyl, oleoyl phenyl-CO—, substituted phenyl-CO—, benzyl-CO— and (substituted benzyl)-CO—. Examples of alkoxy carbonyl and aryloxy carbonyl groups include CH3-O—CO—, (ethyl)-O—CO—, n-propyl-O—CO—, iso-propyl-O—CO—, n-butyl-O—CO—, sec-butyl-O—CO—, t-butyl-O—CO—, phenyl-O—CO—, substituted phenyl-O—CO— and benzyl-O—CO—, (substituted benzyl)-O—CO—. Adamantan, naphtalen, myristoleyl, tuluen, biphenyl, cinnamoyl, nitrobenzoy, toluoyl, furoyl, benzoyl, cyclohexane, norbornane, Z-caproic. In order to facilitate the N-acylation, one to four glycine residues can be present in the N-terminus of the molecule.

The carboxyl group at the C-terminus of the compound can be protected, for example, by an amide (i.e., the hydroxyl group at the C-terminus is replaced with —NH$_2$, —NHR$_2$ and —NR$_2$R$_3$) or ester (i.e. the hydroxyl group at the C-terminus is replaced with —OR$_2$). R$_2$ and R$_3$ are independently an aliphatic, substituted aliphatic, benzyl, substituted benzyl, aryl or a substituted aryl group. In addition, taken together with the nitrogen atom, R$_2$ and R$_3$ can form a C4 to C8 heterocyclic ring with from about 0-2 additional heteroatoms such as nitrogen, oxygen or sulfur. Examples of suitable heterocyclic rings include piperidinyl, pyrrolidinyl, morpholino, thiomorpholino or piperazinyl. Examples of C-terminal protecting groups include —NH$_2$, —NHCH$_3$, —N(CH$_3$)$_2$, —NH(ethyl), —N(ethyl)$_2$, —N(methyl) (ethyl), —NH(benzyl), —N(C1-C4 alkyl)(benzyl), —NH(phenyl), —N(C1-C4 alkyl) (phenyl), —OCH$_3$, —O-(ethyl), —O-(n-propyl), —O-(n-butyl), —O-(iso-propyl), —O-(sec-butyl), —O-(t-butyl), —O-benzyl and —O-phenyl.

The peptides of the present invention may also comprise non-amino acid moieties, such as for example, hydrophobic moieties (various linear, branched, cyclic, polycyclic or heterocyclic hydrocarbons and hydrocarbon derivatives) attached to the peptides; various protecting groups, especially where the compound is linear, which are attached to the compound's terminals to decrease degradation. Chemical (non-amino acid) groups present in the compound may be included in order to improve various physiological properties such; decreased degradation or clearance; decreased repulsion by various cellular pumps, improve immunogenic activities, improve various modes of administration (such as attachment of various sequences which allow penetration through various barriers, through the gut, etc.); increased specificity, increased affinity, decreased toxicity and the like.

According to one embodiment, the peptides of the present invention are attached to a sustained-release enhancing agent. Exemplary sustained-release enhancing agents include, but are not limited to hyaluronic acid (HA), alginic acid (AA), polyhydroxyethyl methacrylate (Poly-HEMA), polyethylene glycol (PEG), glyme and polyisopropylacrylamide.

Attaching the amino acid sequence component of the peptides of the invention to other non-amino acid agents may be by covalent linking, by non-covalent complexion, for example, by complexion to a hydrophobic polymer, which can be degraded or cleaved producing a compound capable of sustained release; by entrapping the amino acid part of the peptide in liposomes or micelles to produce the final peptide of the invention. The association may be by the entrapment of the amino acid sequence within the other component (liposome, micelle) or the impregnation of the amino acid sequence within a polymer to produce the final peptide of the invention.

The compounds of the invention may be linear or cyclic (cyclization may improve stability). Cyclization may take place by any means known in the art. Where the compound is composed predominantly of amino acids, cyclization may be via N- to C-terminal, N-terminal to side chain and N-terminal to backbone, C-terminal to side chain, C-terminal to backbone, side chain to backbone and side chain to side chain, as well as backbone to backbone cyclization. Cyclization of the peptide may also take place through non-amino acid organic moieties comprised in the peptide.

The peptides of the present invention can be biochemically synthesized such as by using standard solid phase techniques. These methods include exclusive solid phase synthesis, partial solid phase synthesis methods, fragment condensation, classical solution synthesis. Solid phase polypeptide synthesis procedures are well known in the art and further described by John Morrow Stewart and Janis Dillaha Young, Solid Phase Polypeptide Syntheses (2nd Ed., Pierce Chemical Company, 1984).

Synthetic peptides can be purified by preparative high performance liquid chromatography [Creighton T. (1983) Proteins, structures and molecular principles. WH Freeman and Co. N.Y.] and the composition of which can be confirmed via amino acid sequencing.

Recombinant techniques may also be used to generate the peptides of the present invention. To produce a peptide of the present invention using recombinant technology, a polynucleotide encoding the peptide of the present invention is ligated into a nucleic acid expression vector, which comprises the polynucleotide sequence under the transcriptional control of a cis-regulatory sequence (e.g., promoter sequence) suitable for directing constitutive, tissue specific or inducible transcription of the polypeptides of the present invention in the host cells.

In addition to being synthesizable in host cells, the polypeptide of the present invention can also be synthesized using in vitro expression systems. These methods are well known in the art and the components of the system are commercially available.

Since the peptides of the present invention comprise anti-bacterial properties they may be used to kill bacteria.

Thus, according to another aspect of the invention there is provided a method of killing bacteria, the method comprising contacting the bacteria with an isolated peptide comprising no more than ten amino acids, having a consensus amino acid sequence $X_1X_2X_3X_4X_5$, wherein $X_1$ and $X_5$ comprise polar amino acids, the peptide having anti-bacterial activity.

The peptides of the present invention have been shown to comprise antibacterial properties in the presence and absence of MazF. Therefore, the present invention contemplates killing of all gram positive and gram negative bacteria, with the peptides of the present invention, although it will be appreciated that they may be particularly effective at killing bacteria which comprise the MazEF module. Such bacteria have been described herein above.

The term "Gram-positive bacteria" as used herein refers to bacteria characterized by having as part of their cell wall structure peptidoglycan as well as polysaccharides and/or teichoic acids and are characterized by their blue-violet color reaction in the Gram-staining procedure. Representative Gram-positive bacteria include: *Actinomyces* spp., *Bacillus anthracis, Bifidobacterium* spp., *Clostridium botulinum, Clostridium perfringens, Clostridium* spp., *Clostridium tetani, Corynebacterium diphtheriae, Corynebacterium jeikeium, Enterococcus faecalis, Enterococcus faecium, Erysipelothrix rhusiopathiae, Eubacterium* spp., *Gardnerella vaginalis, Gemella morbillorum, Leuconostoc* spp., *Mycobacterium abcessus, Mycobacterium avium complex, Mycobacterium chelonae, Mycobacterium fortuitum, Mycobacterium haemophilium, Mycobacterium kansasii, Mycobacterium leprae, Mycobacterium marinum, Mycobacterium scrofulaceum, Mycobacterium smegmatis, Mycobacterium terrae, Mycobacterium tuberculosis, Mycobacterium ulcerans, Nocardia* spp., *Peptococcus niger, Peptostreptococcus* spp., *Proprionibacterium* spp., *Staphylococcus aureus, Staphylococcus auricularis, Staphylococcus capitis, Staphylococcus cohnii, Staphylococcus epidermidis, Staphylococcus haemolyticus, Staphylococcus hominis, Staphylococcus lugdanensis, Staphylococcus saccharolyticus, Staphylococcus saprophyticus, Staphylococcus schleiferi, Staphylococcus similans, Staphylococcus warneri, Staphylococcus xylosus, Streptococcus agalactiae* (group B *streptococcus*), *Streptococcus anginosus, Streptococcus bovis, Streptococcus canis, Streptococcus equi, Streptococcus milleri, Streptococcus mitior, Streptococcus mutans, Streptococcus pneumoniae, Streptococcus pyogenes* (group A *streptococcus*), *Streptococcus salivarius, Streptococcus sanguis*.

The term "Gram-negative bacteria" as used herein refer to bacteria characterized by the presence of a double membrane surrounding each bacterial cell. Representative Gram-negative bacteria include *Acinetobacter calcoaceticus, Actinobacillus actinomycetemcomitans, Aeromonas hydrophila, Alcaligenes xylosoxidans, Bacteroides, Bacteroides fragilis, Bartonella bacilliformis, Bordetella* spp., *Borrelia burgdorferi, Branhamella catarrhalis, Brucella* spp., *Campylobacter* spp., *Chalmydia pneumoniae, Chlamydia psittaci, Chlamydia trachomatis, Chromobacterium violaceum, Citrobacter* spp., *Eikenella corrodens, Enterobacter aerogenes, Escherichia coli, Flavobacterium meningosepticum, Fusobacterium* spp., *Haemophilus influenzae, Haemophilus* spp., *Helicobacter pylori, Klebsiella* spp., *Legionella* spp., *Leptospira* spp., *Moraxella catarrhalis, Morganella morganii, Mycoplasma pneumoniae, Neisseria gonorrhoeae, Neisseria meningitidis, Pasteurella multocida, Plesiomonas shigelloides, Prevotella* spp., *Proteus* spp., *Providencia rettgeri, Pseudomonas aeruginosa, Pseudomonas* spp., *Rickettsia prowazekii, Rickettsia rickettsii, Rochalimaea* spp., *Salmonella* spp., *Salmonella typhi, Serratia marcescens, Shigella* spp., *Treponema carateum, Treponema pallidum, Treponema pallidum endemicum, Treponema pertenue, Veillonella* spp., *Vibrio cholerae, Vibrio vulnificus, Yersinia enterocolitica, Yersinia pestis.*

As used herein the term "contacting" refers to the positioning of the peptides of the present invention such that they are in direct or indirect contact with the bacterial cells. Thus, the present invention contemplates both applying the peptides of the present invention to a desirable surface and/or directly to the bacterial cells.

Contacting the peptides with a surface can be effected using any method known in the art including spraying, spreading, wetting, immersing, dipping, painting, ultrasonic welding, welding, bonding or adhering. The peptides of the present invention may be attached as monolayers or multiple layers.

The present invention coating a wide variety of surfaces with the peptides of the present invention including fabrics, fibers, foams, films, concretes, masonries, glass, metals, plastics, polymers, and like.

An exemplary solid surface that may be coated with the peptides of the present invention is an intracorporial or extracorporial medical device or implant.

An "implant" as used herein refers to any object intended for placement in a human body that is not a living tissue. The implant may be temporary or permanent. Implants include naturally derived objects that have been processed so that their living tissues have been devitalized. As an example, bone grafts can be processed so that their living cells are removed (acellularized), but so that their shape is retained to serve as a template for ingrowth of bone from a host. As another example, naturally occurring coral can be processed to yield hydroxyapatite preparations that can be applied to the body for certain orthopedic and dental therapies. An implant can also be an article comprising artificial components.

Thus, for example, the present invention therefore envisions coating vascular stents with the peptides of the present invention. Another possible application of the peptides of the present invention is the coating of surfaces found in the medical and dental environment.

Surfaces found in medical environments include the inner and outer aspects of various instruments and devices, whether disposable or intended for repeated uses. Examples include the entire spectrum of articles adapted for medical use, including scalpels, needles, scissors and other devices used in invasive surgical, therapeutic or diagnostic procedures; blood filters, implantable medical devices, including artificial blood vessels, catheters and other devices for the removal or delivery of fluids to patients, artificial hearts, artificial kidneys, orthopedic pins, plates and implants; catheters and other tubes (including urological and biliary tubes, endotracheal tubes, peripherably insertable central venous catheters, dialysis catheters, long term tunneled central venous catheters peripheral venous catheters, short term central venous catheters, arterial catheters, pulmonary catheters, Swan-Ganz catheters, urinary catheters, peritoneal catheters), urinary devices (including long term urinary devices, tissue bonding urinary devices, artificial urinary sphincters, urinary dilators), shunts (including ventricular or arterio-venous shunts); prostheses (including breast implants, penile prostheses, vascular grafting prostheses, aneurysm repair devices, heart valves, artificial joints, artificial larynxes, otological implants), anastomotic devices, vascular catheter ports, clamps, embolic devices, wound drain tubes, hydrocephalus shunts, pacemakers and implantable defibrillators, and the like. Other examples will be readily apparent to practitioners in these arts.

Surfaces found in the medical environment include also the inner and outer aspects of pieces of medical equipment, medical gear worn or carried by personnel in the health care setting. Such surfaces can include counter tops and fixtures in areas used for medical procedures or for preparing medical apparatus, tubes and canisters used in respiratory treatments, including the administration of oxygen, of solubilized drugs in nebulizers and of anesthetic agents. Also included are those surfaces intended as biological barriers to infectious organisms in medical settings, such as gloves, aprons and faceshields. Commonly used materials for biological barriers may be latex-based or non-latex based. Vinyl is commonly used as a material for non-latex surgical gloves. Other such surfaces can include handles and cables for medical or dental equipment not intended to be sterile. Additionally, such surfaces can include those non-sterile external surfaces of tubes and other apparatus found in areas where blood or body fluids or other hazardous biomaterials are commonly encountered.

Other surfaces related to health include the inner and outer aspects of those articles involved in water purification, water storage and water delivery, and those articles involved in food processing. Thus the present invention envisions coating a solid surface of a food or beverage container to extend the shelf life of its contents.

Surfaces related to health can also include the inner and outer aspects of those household articles involved in providing for nutrition, sanitation or disease prevention. Examples can include food processing equipment for home use, materials for infant care, tampons and toilet bowls.

According to another embodiment the surface is comprised in a biological tissue, such as for example, mammalian tissues e.g. the skin.

It will be appreciated that the contacting may also be effected in vivo (i.e. within a mammalian body) or ex vivo (i.e. in cells removed from the body). Accordingly, the present invention contemplates administering of the peptides per se (or pharmaceutical compositions comprising same) to subjects in need thereof in order to prevent or treat infections in the body.

As mentioned, the pharmaceutical compositions of the present invention may be administered to a subject in need thereof in order to prevent or treat a bacterial infection.

As used herein, the term "subject in need thereof" refers to an animal including fish, poultry and mammals, preferably the subject is a human subject.

As used herein, the term "treating" refers to curing, reversing, attenuating, alleviating, minimizing, suppressing or halting the deleterious effects of a pathogen infection.

The phrase "pharmaceutical composition", as used herein refers to a preparation of one or more of the active ingredients described herein with other chemical components such as physiologically suitable carriers and excipients. The purpose of a pharmaceutical composition is to facilitate administration of a compound to an organism.

As used herein the term "active ingredient" refers to peptides of the present invention accountable for the intended biological effect. It will be appreciated that a polynucleotide encoding a peptide of the present invention may be administered directly into a subject (as is, or part of a pharmaceutical composition) where it is translated in the target cells i.e. by gene therapy. Accordingly, the phrase "active ingredient" also includes such polynucleotides.

Hereinafter, the phrases "physiologically acceptable carrier" and "pharmaceutically acceptable carrier," which may be used interchangeably, refer to a carrier or a diluent that does not cause significant irritation to an organism and does not abrogate the biological activity and properties of the administered compound. An adjuvant is included under these phrases.

Herein, the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils, and polyethylene glycols.

Techniques for formulation and administration of drugs may be found in the latest edition of "Remington's Pharmaceutical Sciences," Mack Publishing Co., Easton, Pa., which is herein fully incorporated by reference and are further described herein below.

It will be appreciated that the peptides of the present invention can be provided to the individual with additional active agents to achieve an improved therapeutic effect as compared to treatment with each agent by itself.

As mentioned, the peptides of the present invention have been shown to up-regulate the toxic effect of MazF. Therefore the present invention contemplates pharmaceutical compositions comprising other agents capable of up-regulating MazF together with the peptides of the present invention.

Such agents include those that down-regulate mazE. As mentioned, mazE encodes a labile antitoxin that counteracts the action of MazF. *E. coli* mazEF is a stress-induced toxin-antitoxin module. Thus, any stressful condition that prevents the expression of mazEF will lead to a reduction of MazE levels in the cell, permitting the MazF toxin to act.

Exemplary agents capable of down-regulating mazE (and thereby up-regulating the activity of mazF), that may be formulated in the compositions of the present invention include antibiotics (e.g. rifampicin, chloramphenicol and spectinomycin); DNA damaging agents (e.g. mitomycin C., nalidixic acid and trimethoprim); and serine analogues (e.g. serine hydroxamate).

It will be appreciated that treatment of bacterial infections may also comprise providing at the time of administering the peptides of the present invention, stressful conditions, such as UV irradiation in order to down-regulate MazE.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the invention may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions, which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The preparations described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The preparation of the present invention may also be formulated in rectal compositions such as suppositories or retention enemas, using, e.g., conventional suppository bases such as cocoa butter or other glycerides.

The preparation of the present invention may also be formulated as a topical compositions, such as a spray, a cream, a mouthwash, a wipe, a foam, a soap, an oil, a solution, a lotion, an ointment, a paste and a gel.

Pharmaceutical compositions suitable for use in context of the present invention include compositions wherein the active ingredients are contained in an amount effective to achieve the intended purpose. More specifically, a therapeutically effective amount means an amount of active ingredients effective to prevent, alleviate or ameliorate symptoms of disease or prolong the survival of the subject being treated.

Determination of a therapeutically effective amount is well within the capability of those skilled in the art.

For any preparation used in the methods of the invention, the therapeutically effective amount or dose can be estimated initially from in vitro assays. For example, a dose can be formulated in animal models and such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. [See e.g., Fingl, et al., (1975) "The Pharmacological Basis of Therapeutics", Ch. 1 p. 1].

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

As mentioned herein above, the present inventors have also discovered peptides comprising antagonistic properties towards EDF. Such peptides are also referred to herein as EDF antagonists.

It has been recently shown that genes responsible for antibiotic resistance are located on plasmids that also comprise mazEF or other toxin-antitoxin systems [Moritz et al, 2007, PNAS. 104, 311-316]. As indicated in the Background section herein above, toxin-antitoxin systems comprise a pair of genes that specify for two components: the stable toxin and the unstable antitoxin that interferes with the lethal action of the toxin. Plasmids carrying such toxin-antitoxin systems are stabilized in their bacterial host since the toxicity is prevented due to the continuous synthesis of the antitoxin that antagonizes the toxin.

The present inventors have deduced that abrogating the toxicity of the toxin would reduce the need of the bacteria for continuous synthesis of the antitoxin and therefore would lower the advantage for bacteria to comprise the plasmids carrying the antibiotic resistance genes.

Thus, according to another aspect of the present invention, there is provided a method of sensitizing antibiotic-resistant bacterial cells to an antibiotic, the antibiotic-resistant bacterial cells comprising a MazEF system, the method comprising contacting the bacterial cells with an agent capable of reducing the activity of MazF, thereby sensitizing the antibiotic resistant bacterial cells to the antibiotic.

Exemplary antibiotic-resistant bacterial cells include vancomycin-resistant bacterial cells (e.g. vancomycin-resistant enterococci cells) and methecillin-resistant bacterial cells (e.g. methecillin-resistant *Staphylococcus aureus*; MRSA).

Agents capable of reducing the activity of MazF include peptides or small organic molecules. According to one embodiment such agents are EDF antagonists. Candidate EDF antagonists can be identified using an assay system as described in Example 6 (FIG. 15). Those candidates which reduce the anti-bacterial properties of SEQ ID NO: 1 in a significant manner as compared to the properties of EDF administered alone may be considered as positive candidates.

According to one embodiment, the peptides comprise a sequence as set forth in SEQ ID NO: 2 and 6.

It will be appreciated that the EDF antagonists of the present invention may also be used (in combination with an antibiotic) to kill antibiotic-insensitive bacteria. Initially, antibiotic insensitive bacteria are sensitized to the bacteria using the EDF antagonists as described above. After this, the sensitized bacteria may be killed by administration of antibiotics. Alternatively the EDF antagonist and the antibiotics may be administered simultaneously.

Accordingly, the present invention contemplates a kit comprising an EDF antagonist and an antibiotic placed in an appropriate container, and labeled for treatment of an indicated condition.

As used herein the term "about" refers to ±10%.

The terms "comprises", "comprising", "includes", "including", "having" and their conjugates mean "including but not limited to".

The term "consisting of means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Reference is now made to the following examples, which together with the above descriptions illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N.Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

EXAMPLE 1

E. coli mazEF-Mediated Cell Death is Density Dependent

Materials and Methods

Bacterial strains and plasmid: The following sets of *E. coli* strains were used: (i) MC4100relA1 (11), MC4100relA+, (11) and their ΔmazEF::kan derivatives (11) and *E. coli* strain K38 and its ΔmazEF derivative (11); (ii) W3100 and MG1655 (10) and their ΔmazEF::kan derivatives, which we constructed by P1 transduction from strain MC4100relA1 ΔmazEF::kan. pBAD33 carrying chloramphenicol-resistant gene PQE30 (Qiagen) carrying ampicillin-resistant gene. pQE-mazF carrying mazF under the lac promoter (kindly provided by Gad Glaser).

Materials and media: Bacterial cultures were grown in liquid M9 minimal medium with 1% glucose and a mixture of amino acids (10 μg/ml each) (16) and plated on rich LB agar plates as described previously (11). IPTG, nalidixic acid, mitomycin C, trimethoprim, rifampin, chloramphenicol, spectinomycin, and trizma-base were obtained from Sigma (St. Louis, Mo.). Ampicillin was obtained from Biochemie GmbH (Kundl, Austria).

Producing supernatants (SNs) from dense cultures: A culture of an *E. coli* strain that served as an EDF donor was grown at 37° C. for 12 hours in M9 medium with shaking (160 rpm). The cells were diluted 1:100 in M9 medium and grown with shaking (160 rpm) at 37° C. to mid-logarithmic phase ($OD_{600}$=0.6; $2.5 \times 10^8$ cells/ml). Then, cells were centrifuged in 14,000 rpm for 5 minutes. The supernatant was removed and filtered through a 0.22μ filter; the filtrates were stored at 4° C.

mazEF-mediated cell death is dependent on cell density: *E. coli* strains MC4100relA+ and its ΔmazEF derivative were grown to mid-log phase ($OD_{600}$ 0.4-0.6) in M9 medium (containing 0.5% glucose) at 37° C. When the cultures reached a density of $3 \times 10^8$ cells/ml, duplicate 1 ml samples were removed and either not diluted or diluted in pre-warmed M9 medium to densities of $3 \times 10^7$, $3 \times 10^6$, $3 \times 10^5$, or $3 \times 10^4$ cells/ml. To induce mazEF-mediated cell death, samples were incubated without shaking at 37° C. for 10 minutes, and then rifampicin (10 μg/ml) was added to half of the sample ("treated") while the other half served as a control ("untreated"). The samples were further incubated without shaking at 37° C. for 10 minutes and then washed with pre-warmed LB medium at 37° C. The number of colony forming units (CFU) was detected by plating the washed samples on pre-warmed LB plates that were then incubated at 37° C. overnight.

The supernatant of a dense culture can restore mazEF-mediated cell death induced by various stressful conditions: *E. coli* MC4100relA+wt (WT) and MC4100relA+ΔmazEF (ΔmazEF) were grown for 12 hours in M9 medium with shaking (160 rpm) Then, cells were diluted 1:100 in M9 medium and were grown with shaking (160 rpm) at 37° C. to a mid-logarithmic phase ($OD_{600}$=0.6). When the cultures reached a density of $2.5 \times 10^8$ cells/ml, triplicate samples were removed and were either not diluted (Dense), or were diluted to the density of $3 \times 10^4$ cells/ml in pre-warmed M9 medium (M9) or in a pre-warmed supernatant of a dense culture (SN). The samples were incubated without shaking at 37° C. for 10 minutes. Subsequently, these samples were incubated without shaking at 37° C. with (A) Rifampicin (10 μg/ml) for 10 min; (B) Chloramphenicol (50n/m1) for 20 minutes; C) Trimethoprim (2 μg/ml) for 1 hour. Cells were centrifuged in 14,000 rpm for 5 minutes and washed in pre-heated saline. Then, the cells were diluted, plated on LB plates, and incubated at 37° C. for 12 hours. Cell survival was calculated by comparing the colony-forming units (CFUs) of treated cells to those of untreated cells.

Observation of EDF activity in *E. coli* cultures during logarithmic growth and during stationary growth: *E Coli*. MC4100relA+ (WT) serving as an EDF donor were grown for 12 hours in M9 medium with shaking (1600 rpm). Then cells were diluted 1:100 in M9 medium and were grown with shaking (160 rpm) at 37° C. At intervals of 30 minutes, optical density ($OD_{600}$) was measured, and 2 ml of the culture were centrifuged in 14,000 rpm for 5 minutes. The supernatant was removed and filtrated in 0.22μ filters. EDF activity was determined as described in Example 3, herein below.

Results

Figure 2D:
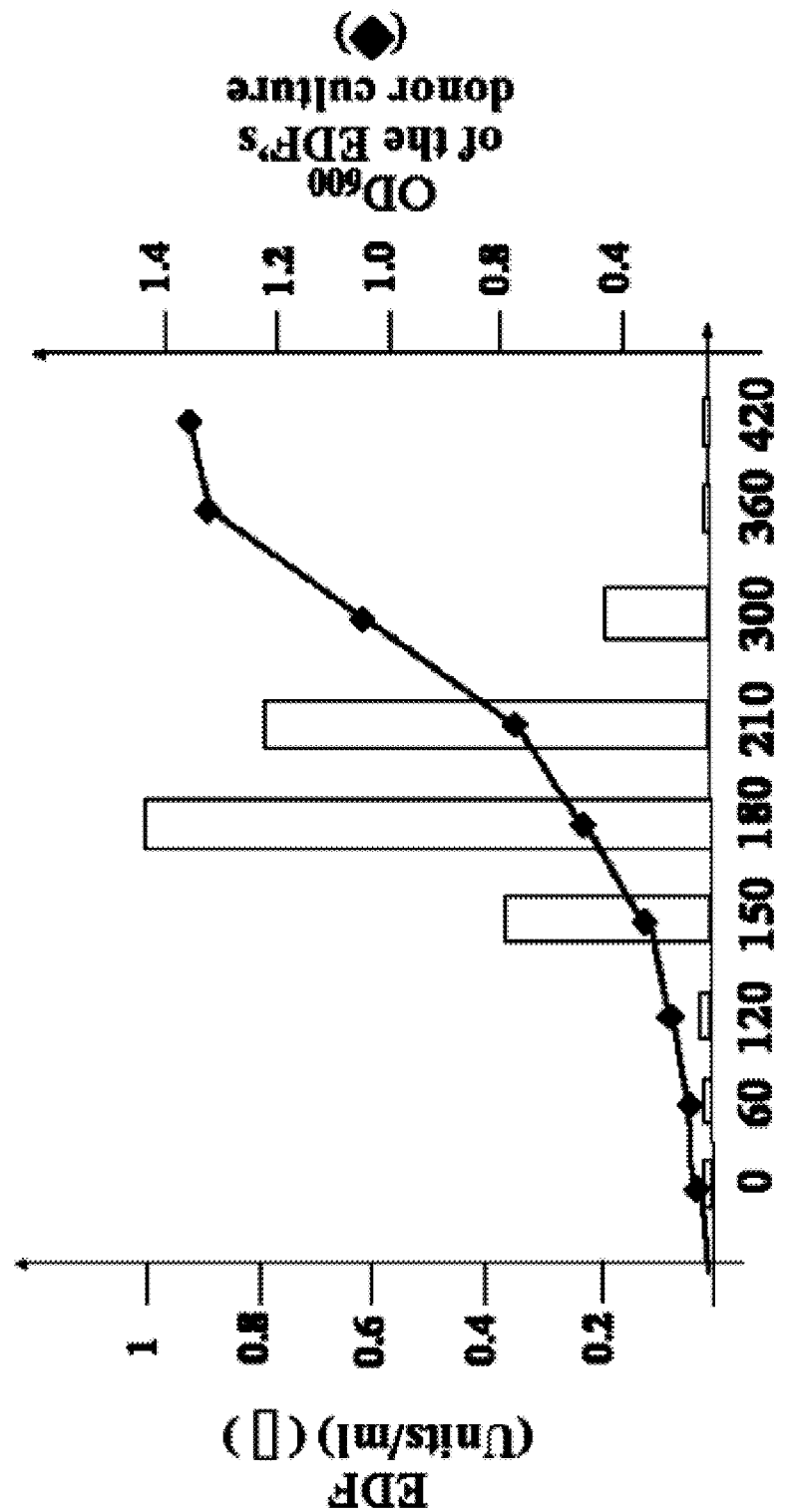
FIG. 2D is a graph illustrating the EDF concentration in the supernatant of the *E. coli* culture at various stages of growth.

It was found that mazEF mediated *E. coli* cell death is dependent on the density of the bacterial culture. Adding rifampicin to shortly inhibit transcription led to mazEF-mediated cell death at densities of $3 \times 10^8$ or $3 \times 10^7$ cells/ml, but not at $3 \times 10^5$ or $3 \times 10^4$ cells/ml (FIG. 1). Similar results were obtained when mazEF-mediated cell death was induced by shortly inhibiting translation with chloramphenicol, or by DNA damage with trimethoprim (data not shown). Consequentially, the present inventors examined whether the supernatant (SN) of a dense culture will restore mazEF-mediated cell death of a diluted culture. To this end, the SN of a dense culture ($2.5 \times 10^8$ cells/ml) was added to a diluted culture ($2.5 \times 10^4$ cells/ml). MazEF-mediated cell death was induced by either rifampicin (FIG. 2A), or chloramphenicol (FIG. 2B), or trimethoprim (FIG. 2C). Cell death was not observed in the diluted cultures to which SN from a concentrated culture was not added (FIGS. 2A-C). Thus, it may be concluded that mazEF-mediated cell death requires an extracellular factor. This factor has been named the "Extracellular Death Factor" (EDF). Note that EDF activity was observed in *E. coli* cultures during logarithmic growth but not during stationary growth (FIG. 2D).

EXAMPLE 2

EDF is a Signal Molecule

Materials and Methods

Strains MC4100relA+/pBAD ($Cam^R$), MC4100relA+/pQE30 ($Cam^S$), and MC4100relA+ΔmazEF/pQE30 ($Cam^S$) were each grown separately in M9 minimal medium containing the relevant antibiotic. When the cultures reached mid-logarithmic phase (OD=0.4), they were washed, and resuspended in M9 minimal medium. A first mixture of two strains was prepared in M9 medium such that the final concentrations were $10^8$ cells/ml of a "donor" $Cam^R$ culture (carrying $Cam^R$/pBAD) and $10^4$ cells/ml of an "acceptor" $Cam^S Amp^R$ culture (wild type or ΔmazEF carrying $Amp^R$ pQE30). A second mixture comprising the above described strains was prepared in M9 in which the final concentrations of the strains were $10^4$ cells/ml:$10^4$ cell/ml.

At various times, samples were removed, and pre-incubated without shaking at 37° C. for 10 min, after which chloramphenicol (45 μg/ml) was added to induce cell death. A culture to which no chloramphenicol was added served as a control. The cultures were washed and resuspended in pre-heated (37° C.) saline. CFUs were determined by plating on LB+Cam and LB+Amp plates that were then incubated at 37° C. for 12 hrs.

Effect of pH on EDF: Supernatants from the "donor" cultures described above were incubated at pH 3, 5, 7, 9 or 11 for 2 hours and titrated to PH 7. Their ability to restore mazEF-mediated cell death to a diluted culture was determined as described above.

Effect of temperature on EDF: Supernatants from the "donor" cultures described above were incubated at 37° C., 60° C., 80° C., or 100° C. for 10 minutes and cooled to 37° C. Their ability to restore mazEF-mediated cell death to a diluted culture was determined as described above.

Effect of proteinase K on EDF: Supernatants from the "donor" cultures described above were incubated with shaking at 37° C. for 2 hours as such or with agarose bease or with proteinase K-agarose beads. The beads were then removed by centrifugation at 14,000 rpm for 10 minutes. Their ability to restore mazEF-mediated cell death to a diluted culture was determined as described above.

Results

Figure 3A:
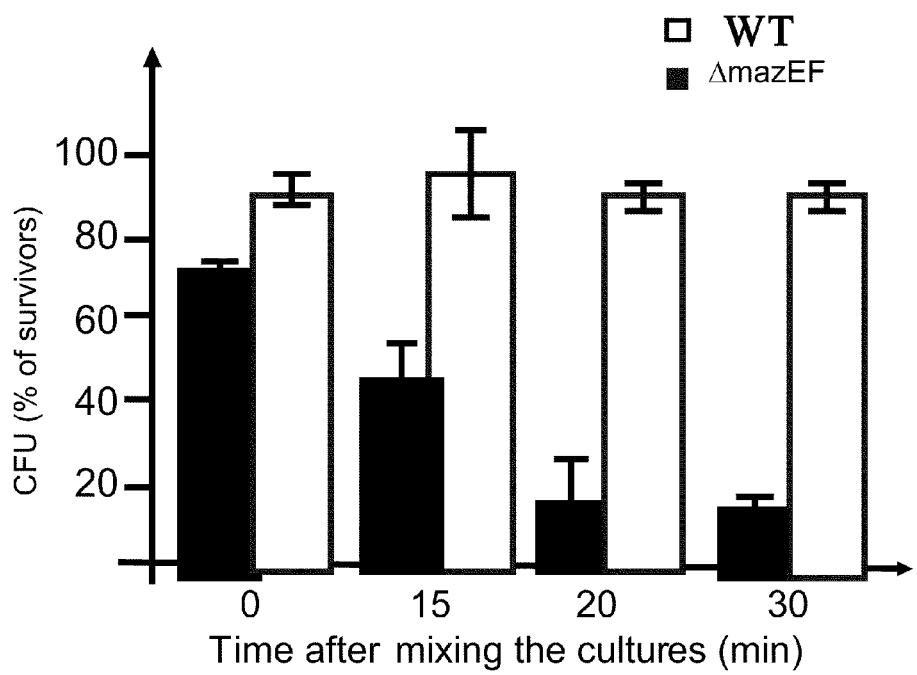
FIGS. 3A-B are bar graphs illustrating that EDF is a signal molecule that can trigger mazEF-mediated cell death.
Figure 3B:
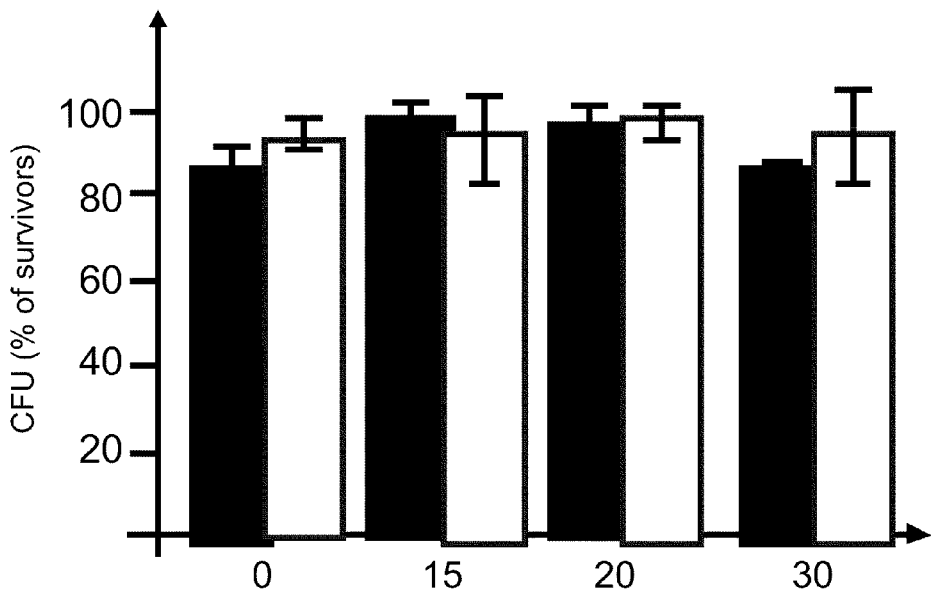

Based on the observation that a brief induction with chloramphenicol causes mazEF-mediated cell death (FIG. 2B), a new experimental system was constructed in which equal volumes of two cultures of E. coli strain MC4100relA$^+$ were mixed: a dense culture of MC4100relA$^+$Cam$^R$, to serve as the EDF "donor", and a diluted culture of MC4100relA$^+$Cam$^S$, to serve as the EDF "recipient". It was predicted that in the presence of EDF produced by the "donor" sub-population, chloramphenicol would trigger mazEF-mediated cell death in the Cam$^S$ recipient sub-population, while not killing the Cam$^R$ "donor" sub-population. Indeed, in the presence of chloramphenicol, mazEF-dependent cell death in the Cam$^S$ cells from the dilute culture was observed (FIGS. 3A-B). These results suggest that the EDF produced by the dense, Cam$^R$ sub-population could act as a signal molecule for the death of cells in the diluted, Cam$^S$ sub-population.

Figure 3C:
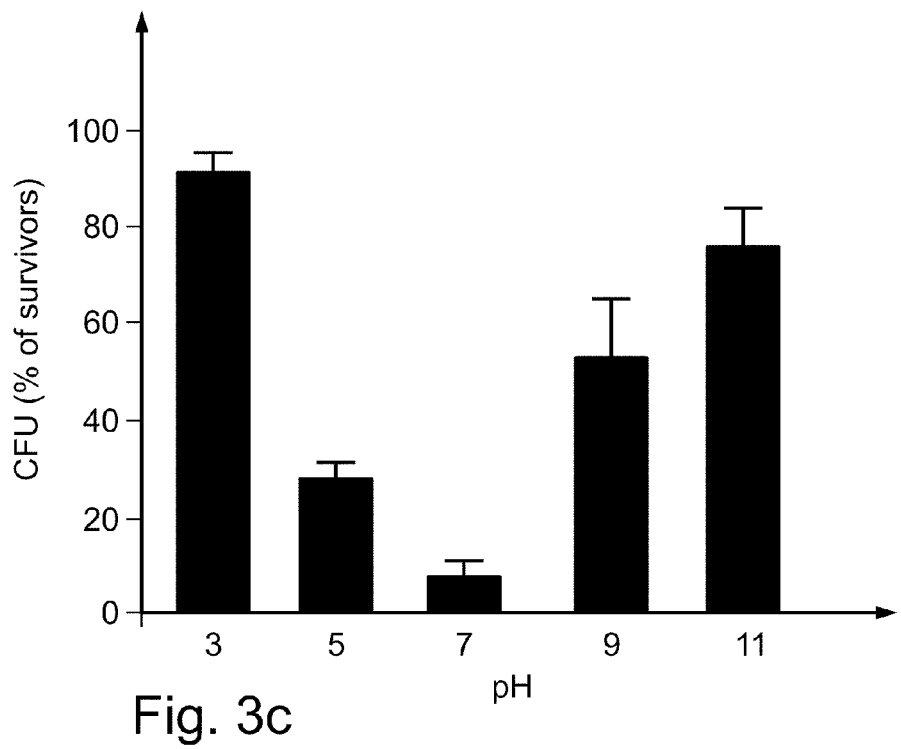
FIGS. 3C-E are graphs illustrating the effect of pH (FIG. 3C), the effect of temperature (FIG. 3D) and the effect of proteinase K (FIG. 3E) on EDF.
Figure 3D:
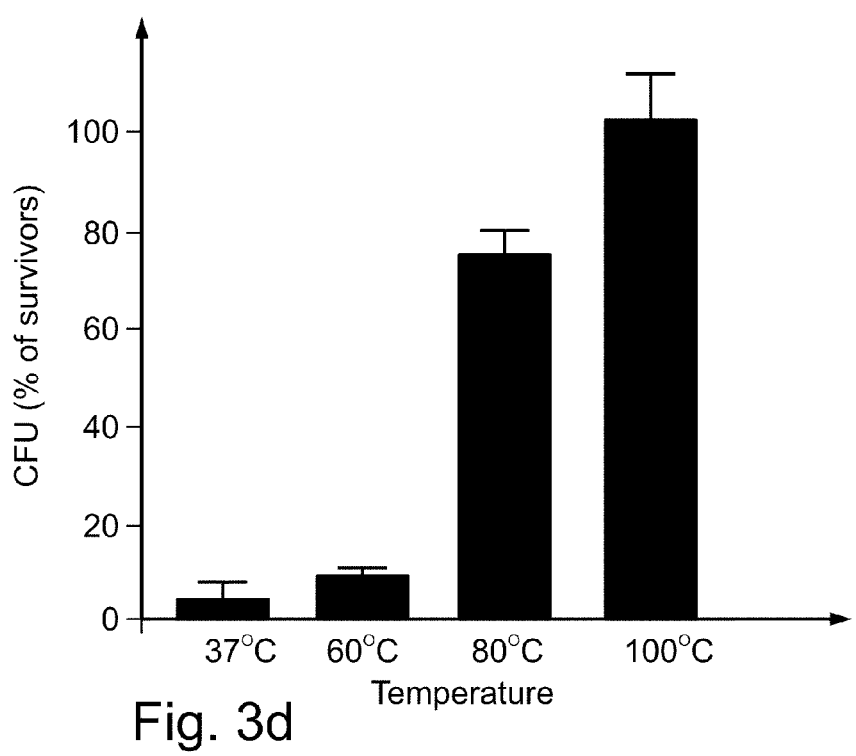
Figure 3E:
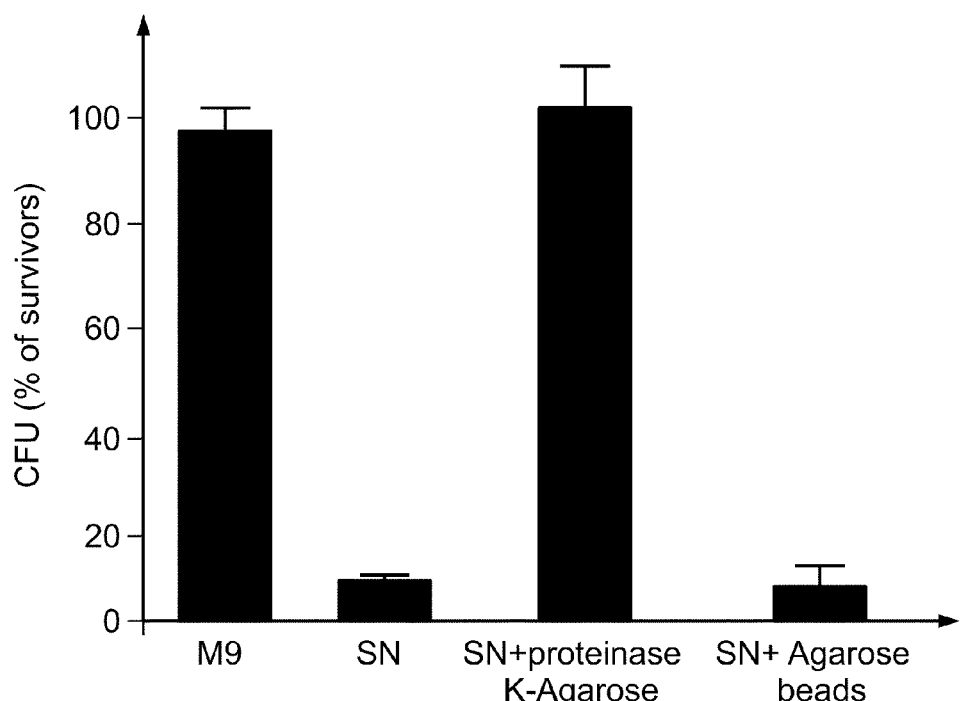

Preliminary characterization of EDF revealed that it is sensitive to extreme pH (FIG. 3C), high temperature (80° C. to 100° C.; FIG. 3D) and proteinase K (FIG. 3E)

EXAMPLE 3

MazEF Affects Both EDF Production and Response

Materials and Methods

Quantification of EDF activity: The supernatant of MC4100relA$^+$ (dense culture of 2.5×10$^8$ cells/ml), serving as a donor, was titrated for EDF activity at different dilutions in Tris-buffer (pH 7.0). A diluted culture (2.5×10$^4$ cells/ml) of MC4100relA$^+$ served as a recipient. A dilution factor of 25 (which is found in the linear range of the curve) permits 70% loss of viability. Therefore, one unit of EDF corresponds to a dilution factor of 25.

Measuring the effect of various stressful conditions on EDF production: E. coli MC4100relA$^+$wt was grown in M9 to a mid-logarithmic phase (OD$_{600}$=0.6) as described in Example 1. The cells were incubated for 10 minutes without shaking and one of the following stressful conditions was applied: i) incubation at 37° C. with: chloramphenicol (45 μg/ml) for 20 minutes (Cm), rifampicin (20 μg/ml) (Rif), nalidixic acid (1000 μg/ml) (Nal), or mitomycin C (0.25 μg/ml) (Mit) for 10 minutes, trimethoprim (2 μg/ml) for 1 hr (Tm); ii) 10 min at 50° C.; and iii) Over-expression of MazF (MazF). MC4100relA/pQEmazF was induced with IPTG (1 mM) at 37° C. for 30 minutes. SNs were obtained as described in Example 1. The SNs from cultures that were induced by antibiotic were dialyzed in Tris-buffer (1 mM) for 8 hours at 24° C., followed by 12 hours at 4° C. The EDF activities of the SNs were quantified as described herein above. The SN of an untreated culture (NT) served as a control.

EDF response is mazEF dependent: E. coli MC4100relA$^+$ (WT) and MC4100relA$^+$ΔmazEF (AmazEF) were grown to a mid-logarithmic phase (OD$_{600}$=0.6) as described in Example 1. When the cultures reached a density of 2.5×10$^8$/ml, duplicate samples were removed and diluted in pre-heated M9 medium to a density of 2.5×10$^4$/ml. To these diluted samples of recipient cells were added various concentrations of the SN obtained from a dense culture of E. coli MC4100relA$^+$/pQE-mazF (+MazF) as described herein above. Subsequently samples were incubated without shaking at 37° C. with rifampicin (10 μg/ml).

Killing of E. coli cells by chemically synthesized EDF in combination with other antibiotic: E. coli MC4100relA$^+$wt (WT) and MC4100relA$^+$ΔmazEF (ΔmazEF) were grown for 12 hours in M9 medium with shaking (160 rpm). Then, cells were diluted 1:100 in M9 medium and were grown with shaking (160 rpm) at 37° C. to a mid-logarithmic phase (OD$_{600}$=0.6). Duplicate samples were removed from the cultures at a density of 2.5×10$^8$ (Dense), diluted in pre-heated M9 medium to the density of 3×10$^4$ (M9) or diluted in pre-heated M9 applied with different concentrations of EDF. The samples were incubated for 10 minutes at 37° C. without shaking Then rifampicin (10 μg/ml) was added and the cells were incubated for 10 minutes without shaking. The cells were centrifuged in 14000 rpm for 5 minutes and washed in pre-heated saline. Then, the cells were diluted, plated on LB plates and incubated at 37° C. for 12 hours. Cell killing was calculated by comparing the number of the colony-forming ability of cells treated by stressful conditions to those of the cells that were not exposed to the treatment.

Killing of E. coli cells by chemically synthesized EDF itself: E. coli MC4100relA$^+$wt (WT) and MC4100relA$^+$Δmaz EF (ΔmazEF) were grown for 12 hours in M9 medium with shaking (160 rpm). Then, cells were diluted 1:100 in M9 medium and were grown with shaking (160 rpm) at 37° C. to a mid-logarithmic phase (OD$_{600}$=0.6). Samples were removed from the cultures at a density of 2.5×10$^8$ (Dense), centrifuged in 14000 rpm for 5 minutes and washed in pre-heated M9. The samples were applied with different concentrations of EDF, incubated for 3 hours at 37° C. without shaking. Then, cells were centrifuged in 14000 rpm for 5 minutes and washed in pre-heated saline. Then, the cells were diluted, plated on LB plates and incubated at 37° C. for 12 hours. Cell killing was calculated by comparing the number of the colony-forming ability of cells treated by stressful conditions to those of the cells that were not exposed to the treatment.

Results

Figure 4:
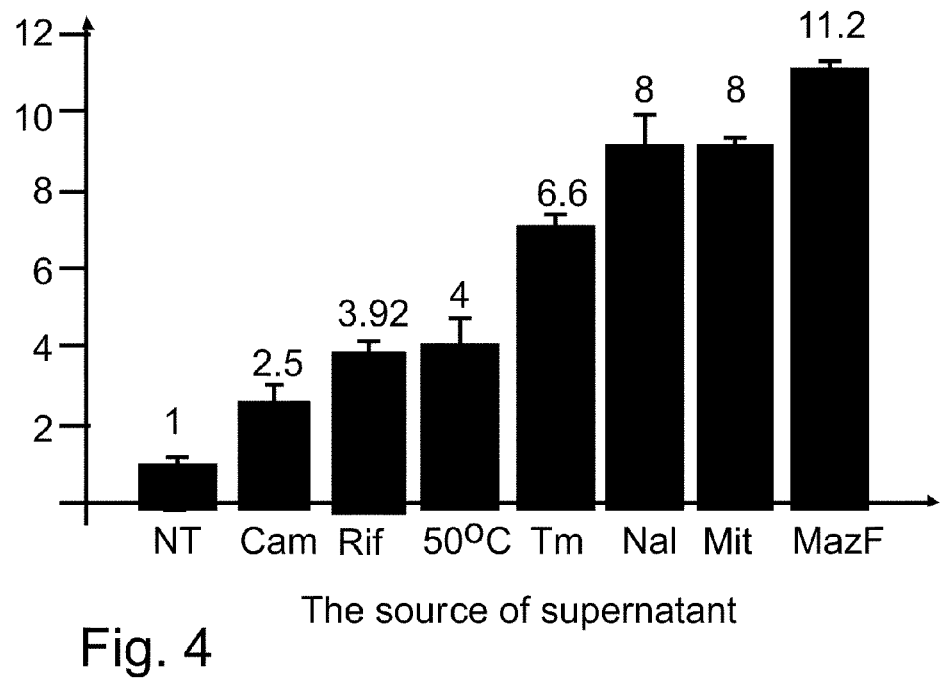
FIG. 4 is a bar graph illustrating the effect of various stressful conditions on EDF production.

In order to compare the EDF activities of the SNs of dense cultures that had been subjected to various stressful conditions, an assay was developed that permits the quantification of EDF activity in a particular SN. This assay compares the dilution factor of the SN that permits 70% loss of viability of MC4100relA$^+$ (WT) that serves as a recipient (diluted culture). The mazEF module was triggered by subjecting the donor strain MC4100relA$^+$ (dense culture) to various specific stressful conditions, and then determined the resulting levels of EDF production by measuring the EDF activity of its SN. As shown, the level of EDF is significantly increased by all applied stressful conditions, although not at the same level (FIG. 4). Inducing mazEF by submitting the cultures to high temperature or to the chemical inhibitors of transcription and/or translation rifampicin or chloramphenicol led to an intermediate level (2.5 to 4.0 units/ml) of EDF production. Inducing mazEF by submitting the cultures to the DNA damaging agents trimethoprim, nalidixic acid, or mitomycin C led to high level (6.6 to 8.0 units/ml) of EDF production (FIG. 4). Overproducing MazF from a plasmid led to the highest level (11.0 units/ml) of EDF production (FIG. 4). Thus, the activation of mazEF causes a significant increase in EDF production.

Figure 5:
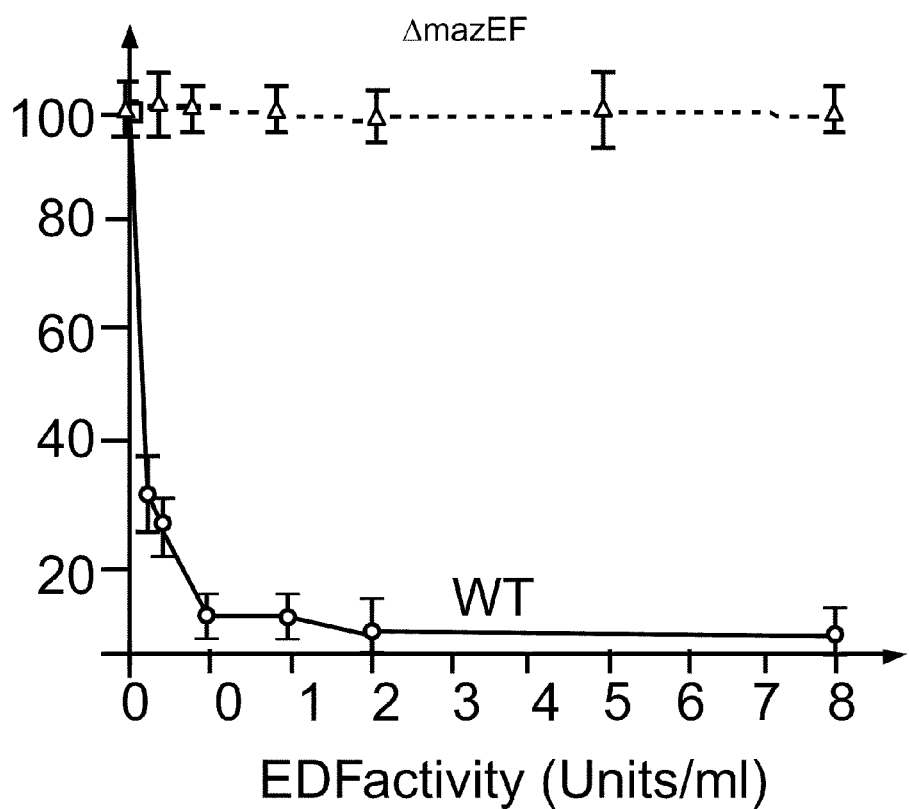
FIG. 5 is a graph illustrating that the EDF response is mazEF dependent.
Figure 6:
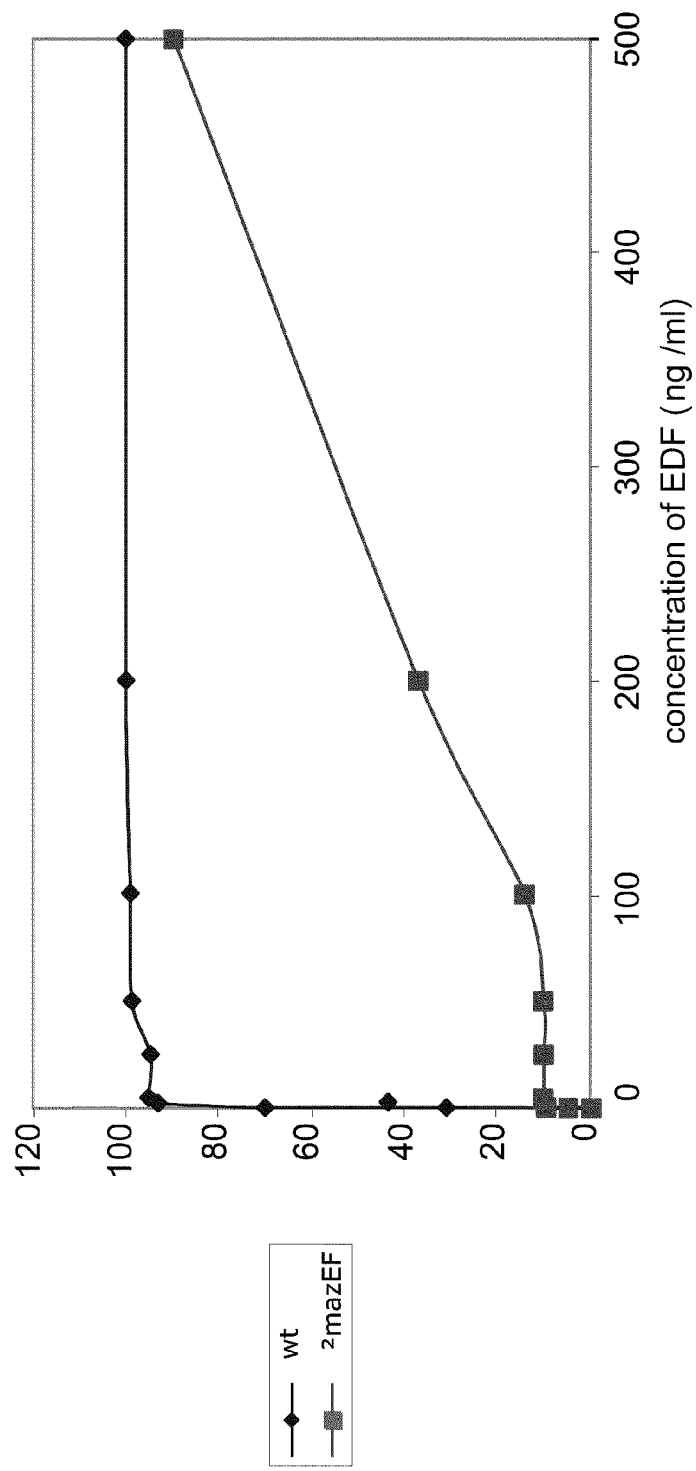
FIG. 6 is a graph illustrating that killing of E. coli cells by chemically synthesized EDF in combination with other antibiotic.
Figure 7:
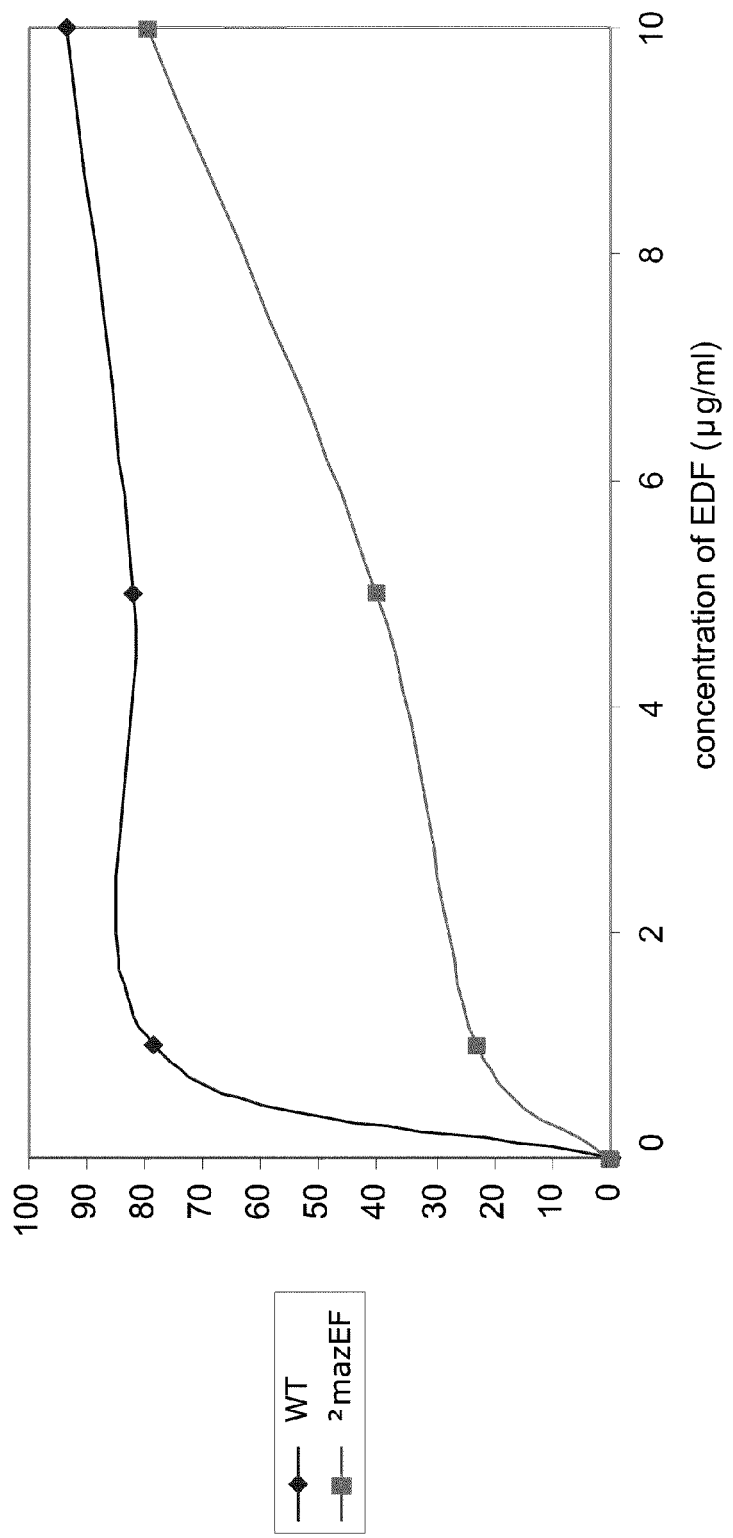
FIG. 7 is a graph illustrating killing of E. coli cells by chemically synthesized EDF itself.

In order to examine whether the response to high concentrations of EDF is also affected by the mazEF module, diluted cultures of E. coli MC4100relA$^+$ (WT) and its ΔmazEF derivative were exposed to various dilutions of supernatants from a dense culture of MC4100relA$^+$ in which mazF was over-expressed. It was found that the response to EDF was completely dependent on mazEF (FIG. 5). However, when chemically synthesized EDF was used (NNWNN—SEQ ID NO: 1), in conjunction with an antibiotic (rafamycin) a mazEF-dependent cell death was observed at low concentrations of EDF (1-500 ng/ml) (FIG. 6), while at higher concentrations of EDF (over 500 ng/ml) cell death was mazEF-independent. Note that chemically synthesized EDF can induce by itself (without antibiotic) cell death (FIG. 7). Also in this case, cell death is mazEF-dependent at low concentrations of EDF (1-10 µg/ml), and mazEF-independent at higher concentrations of EDF (higher then 10 µg/ml).

EXAMPLE 4

EDF Production and Response in Various E. coli Strains

The following experiment was conducted in order to analyze EDF production and response in dense donor and dilute cultures of E. coli strains, K38, W3110, and MG1655.

Materials and Methods

Comparison of EDF response in MC4100relA$^+$, K38, W3110, and MG1655 E. coli strains: Cultures of MC4100relA$^+$, K38, W3110, and MG1655 E. coli were grown as described in Example 1. When the cultures reached a density of 2.5×10$^8$ cells/ml, duplicate samples were removed and diluted to 3×10$^4$ cells/ml in pre-heated supernatant of a dense culture of MC4100relA$^+$(WT) which had been titrated to have an EDF concentration of either 1 unit/ml or 10 units/ml (quantified as described in Example 3). After incubation without shaking at 37° C. for 10 minutes, rifampicin (10 µg/ml) was added, and the culture was incubated without shaking at 37° C. for an additional 10 minutes. Cells were centrifuged in 14,000 rpm for 5 minutes and washed in pre-heated saline. Then, the cells were diluted, plated on LB plates, and incubated at 37° C. for 12 hours. Cell survival was calculated by comparing the colony-forming units (CFUs) of treated cells to those of untreated cells.

Comparison of EDF production in different E. coli strains: E. coli strains MC4100relA$^+$, K-38, MG1655, and W3110 were grown to mid-logarithmic phase (OD$_{600}$=0.6) as described in Example 1. SNs of these untreated dense cultures (NT) were obtained and their activity was quantified as described above. SNs were also obtained from cultures of the parallel strains harboring pQE-mazF in which MazF was overproduced (+MazF) which were grown in M9 with added ampicillin to mid-logarithmic phase and mazF was induced. Finally, SNs were obtained and EDF activity was quantified, as described above.

Results

Although EDF activity in both donor and recipient cultures was observed for each of these three strains, some significant differences in strain MG1655 both for the EDF response (Table 3, herein below) and its production (Table 4, herein below) were noted.

TABLE 3

| Strain | % Survival of recipient culture in response to added EDF | |
|---|---|---|
| | EDF 1 units/ml | EDF 10 units/ml |
| MC4100relA$^+$ | 8.0 ± 5.0 | 7.0 ± 2.0 |
| K-38 | 17.0 ± 4.2 | 12.0 ± 6.6 |
| MG1655 | 77.8 ± 3.4 | 19.6 ± 4.5 |
| W3110 | 15.0 ± 3.6 | 14.0 ± 2.3 |

TABLE 4

| Strain | Units of EDF activity from donor cultures | |
|---|---|---|
| | NT | +MazF |
| MC4100relA$^+$ | 1.0 ± 0.2 | 10.0 ± 1.0 |
| K-38 | 1.0 ± 0.5 | 9.5 ± 2.3 |
| MG1655 | 0.2 ± 0.1 | 5.0 ± 1.2 |
| W3110 | 1.0 ± 0.3 | 10.8 ± 1.1 |

In strain MG1655, mazEF-mediated cell death took place only in the presence of extremely high concentrations of EDF (Table 3). Although both MG1655 and W3110 are considered to be the strains most closely related to the E. coli wild type strain, the present inventors found that signaling by EDF was impaired and required very high concentrations of EDF only in strain MG1655 but not in strains W3110.

EXAMPLE 5

EDF Purification and Characterization Thereof

Materials and Methods

Figure 8:
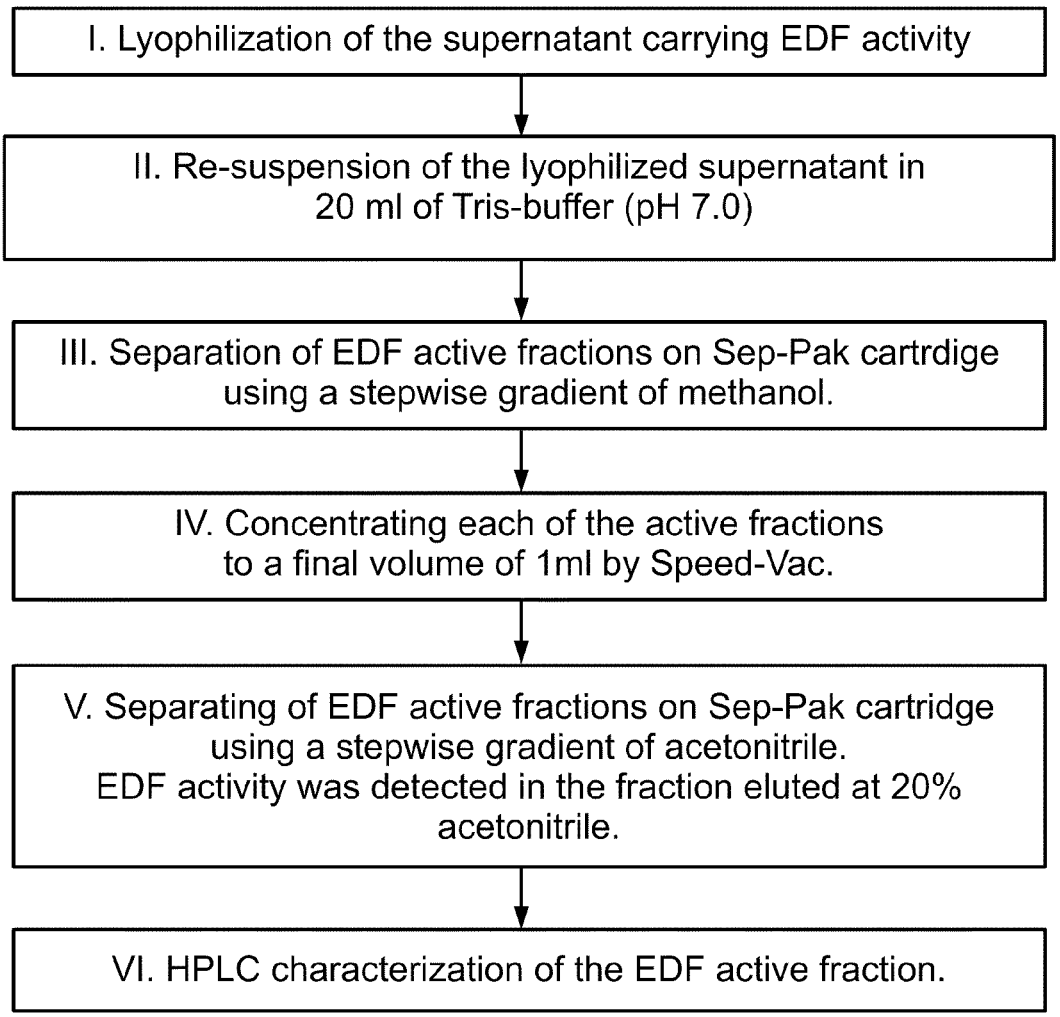
FIG. 8 is a flow diagram illustrating the procedure of EDF purification.

E. coli MC4100relA$^+$wt(WT) cells were grown to mid-log phase in 20 liters of minimal M9 medium with 1% glucose. A cell free culture fluid was prepared by removing the cells from the growth medium by centrifugation, followed by two successive filtrations through 0.22 µm filters. The filtrate was stored overnight at −20° C. The purification steps are illustrated in FIG. 8. The purification steps consisted essentially of 1) Concentration by lypophilization; 2) Re-suspension in 10 ml of 1 mM Tris Buffer pH 7.0; 3) EDF active fractions were separated on a C-18 SepPak cartridge (using a stepwise of 40% to 80% methanol gradient) EDF activity was found in fractions eluted with 40% and 80% methanol; 4) The active fractions were mixed and concentrated by a Speed-Vac; 5) EDF active fractions were separated again on a C-18 Sep-Pak cartridge, but this time a stepwise gradient of 5% to 60% acetonitrile. Fractions that had EDF activity were eluted at 20% acetonitrile; and 6) Active fraction was purified by HPLC chromatography (using a gradient of 2%-98%) acetonitrile at a low rate of 1.3%/min).

Mass spectroscopy analysis (MS): HPLC was carried out under acidic conditions. Milliabsorbance (at 220 nM) determined during elution from the HPLC column of the purified supernatant was carried out with formic acid (pH 2.5).

ESI-MS: In order to investigate the chemical composition of the purified peak found to have EDF activity, ESI-MS was carried out using a QT of 2 Micromass instrument.

Assignment of the proton and carbon signals of EDF by NMR: The assignment of the proton and carbon signals is based on 1D and 2D (COSY, gHSQC, gHMBC, gNOESY) NMR experiments. In the $^1$H NMR spectrum four doublet protons were observed between 8.60 and 7.90 ppm. These protons were assigned as amide protons of the peptide backbone on the basis of their chemical shifts and partial exchange with the water. Eight additional singlet amide protons appeared at 7.41 (4H' s) and 6.85 (1H), 6.80 (1H), 6.79 (1H) and 6.73 (1H) ppm. These signals were assigned to four primary amide groups but did not show any NMR correlations with other protons or carbons in the 2D experiments. The doublet amide proton signals were correlated in the COSY spectrum with the corresponding a-protons of the amino acids (See Table 5 herein below) and the a-protons in turn were correlated with diasereotopic protons of methylene groups (based on the HSQC correlations) three of these fragments were assigned as aspargin units with aid of correlations between the methylene protons to the amide carbonyls. The indole unit of the Trp was assigned on the basis COSy, HSQC and HMBC correlations (see Table 5 herein below). The fifth amino acid presented only the a and b-protons due to the fast exchange of the primary amine protons with the water and thus its assignment began with a-proton. The sequence of the amino acids was assigned on basis of HMBC correlations between the carbonyl of $^1$Asn with the amide proton of $^2$Asn, of $^2$Asn carbonyl with Trp amide proton, of Trp carbonyl with $^3$Asn amid proton and of $^4$Asn carbonyl with $^5$Asn amide proton. The same assignment resulted from interpretation of the NOESY spectrum.

TABLE 5

| Position | | $^d$C, mult. | $^d$H, mult., J (Hz) |
|---|---|---|---|
| $^1$Asn | 1 | 168.5 s | — |
| | 2 | 49.5 d | 4.17 t 6.1 |
| | 3 | 34.5 t | 2.66 d 6.1 |
| | 4 | 172.2 s | — |
| | 2-NH$_2$ | — | b |
| $^2$Asn | 1 | 171.6 s | — |
| | 2 | 50.3 d | 4.65 m |
| | 3 | 35.6 t | 2.55 m |
| | | | 2.65 m |
| | 4 | 174.0 s | — |
| | 2-NH | — | 8.61 d 7.2 |
| $^3$Trp | 1 | 172.6 s | — |
| | 2 | 54.3 d | 4.61 dd 7.8, 6.2 |
| | 3 | 26.3 t | 3.18 dd 14.8, 6.2 |
| | | | 3.27 dd 14.8, 7.8 |
| | 4 | 108.4 s | — |
| | 4a | 126.6 s | — |
| | 5 | 111.6 d | 7.42 d 8.0 |
| | 6 | 121.7 d | 7.19 dd 8.0, 7.4 |
| | 7 | 119.1 d | 7.09 dd 7.8, 7.4 |
| | 8 | 117.4 d | 7.58 d 7.8 |
| | 8a | 135.9 s | — |
| | 9 | 124.3 d | 7.08 brs |
| | 2-NH | — | 8.08 d 7.0 |
| | 8a-NH | — | 10.05 brs |
| $^4$Asn | 1 | 171.2 s | — |
| | 2 | 50.0 d | 4.58 dt 6.3, 7.7 |
| | 3 | 35.9 t | 2.45 dd 13.6, 7.7 |
| | | | 2.55 m |
| | 4 | 174.2 s | — |
| | 2-NH | — | 8.13 d 7.7 |

TABLE 5-continued

| Position | | $^d$C, mult. | $^d$H, mult., J (Hz) |
|---|---|---|---|
| $^5$Asn | 1 | 174.6 s | b |
| | 2 | 49.8 d | 4.51 dt 5.3, 7.8 |
| | 3 | 36.1 t | 2.66 m |
| | | | 2.74 dd 15.8, 5.3 |
| | 4 | 174.1 s | — |
| | 2-NH | — | 7.93 d 7.8 |

$^b$Exchanged with the water.

Table 5 herein above is a table of NMR data of chemically synthesized EDF (4 mg) in 4:1 H$_2$O/D$_2$O (0.5 mg) as measured at 400 MHz for $^1$H and 125 MHz for $^{13}$C.

Chemically synthesized EDF restores mazEF mediated cell death to a dilute culture: E. Coli MC4100relA$^+$ cells, K38 cells and W3110 and ΔmazEF cells were grown as described in Example 1 herein above. At a density of 2.5×10$^8$ cells/ml, samples were either not diluted (dense) or diluted to 3×10$^4$ cells/ml in pre-warmed M9 medium (Diluted culture) or in a pre-warmed M9 applied with chemically synthesized EDF (2.5 ng/ml; diluted culture+EDF). For FIGS. 12A-C, samples were incubated with rifampicin as in FIG. 2A. For FIG. 13A, samples were incubated in trimethorpin (2 μg/ml) for 1 hour and for FIG. 13B samples were incubated in chlorapmphenicol (50 μg/ml) for 20 minutes.

Results

Following HPLC, EDF was eluted at the elution time of 20.5 minutes, as illustrated in FIGS. 9A-B. To avoid damaging EDF in acidic conditions, electrospray ionization mass spectroscopy (ESI-MS) was performed at neutral pH. A peak of 661 Daltons was obtained as illustrated in FIG. 10A. This peak was not observed during standard MS analysis at pH 2.5 (FIG. 11).

Figure 10B:
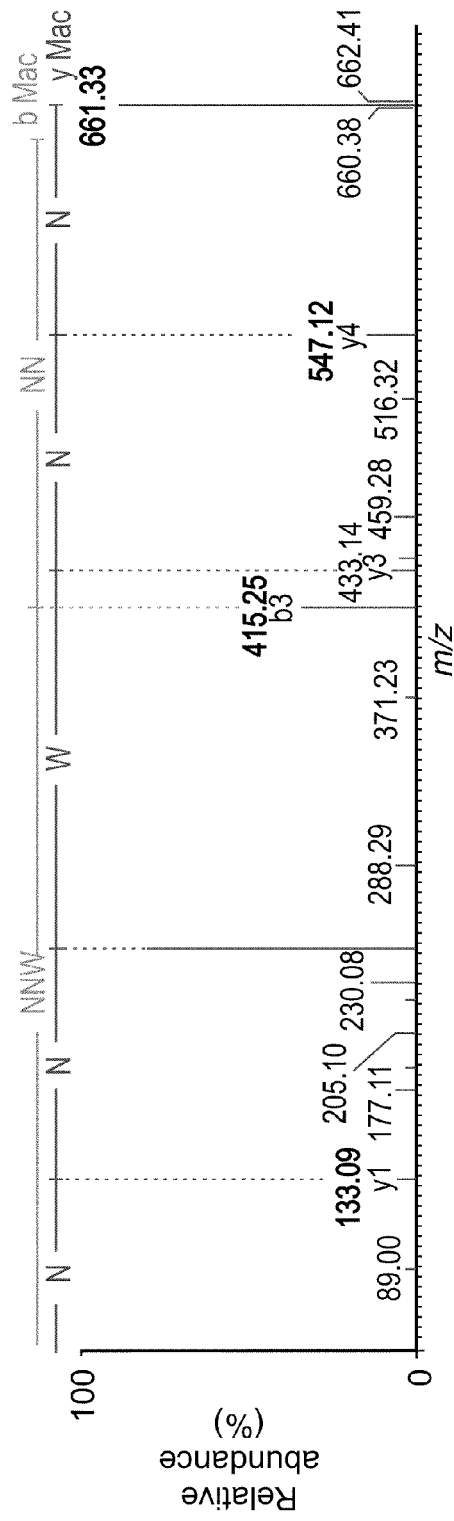
FIG. 10B illustrates the spectrum obtained by MS/MS analysis of the 661 MW peak.
Figure 10C:
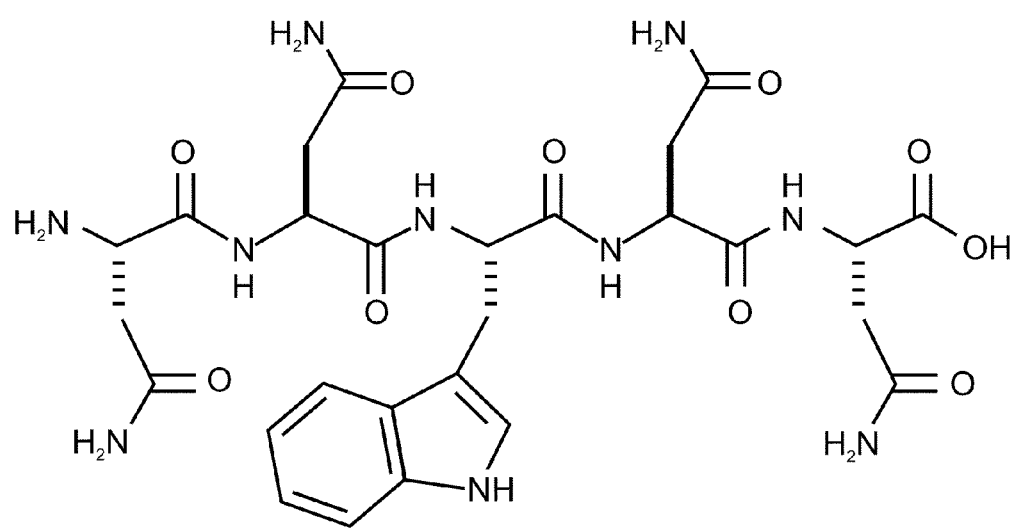
FIG. 10C is a representation of the structure of EDF as determined by nuclear magnetic resonance (NMR) analysis.
Figure 11:
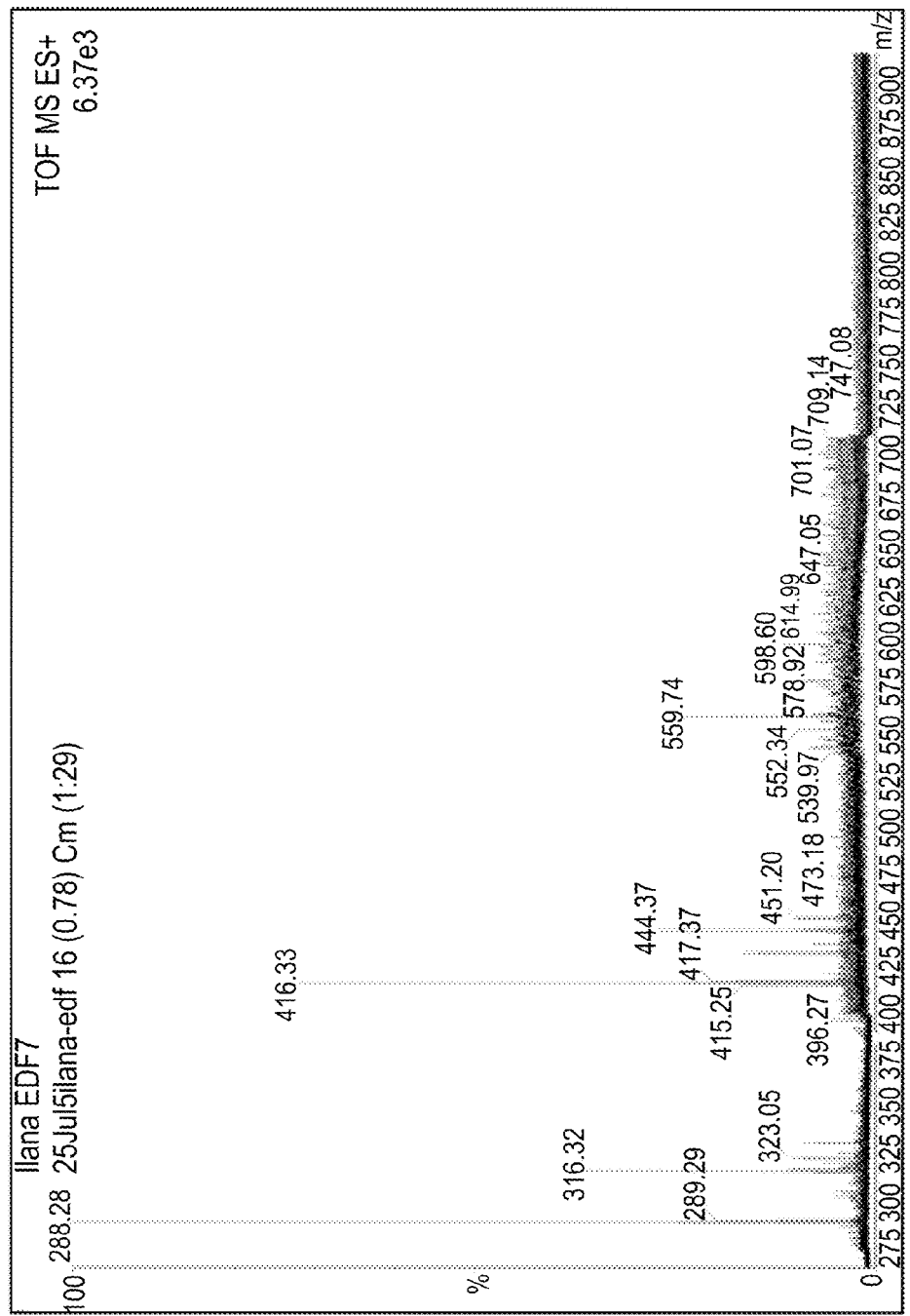
FIG. 11 illustrates the results obtained by HPLC following purification of EDF as described herein.
Figure 12A:
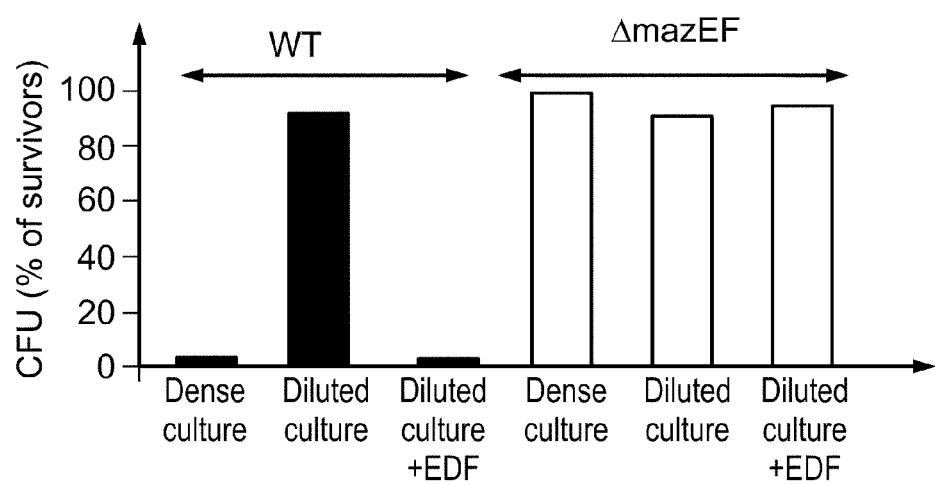
FIGS. 12A-C are bar graphs illustrating that the chemically synthesized EDF can restore mazEF mediated cell death to a diluted culture of MC4100relA$^+$ E. coli (FIG. 12A); K 38 E. coli (FIG. 12B); and W3110 E. Coli (FIG. 12C) induced by rifampimicin.
Figure 12B:
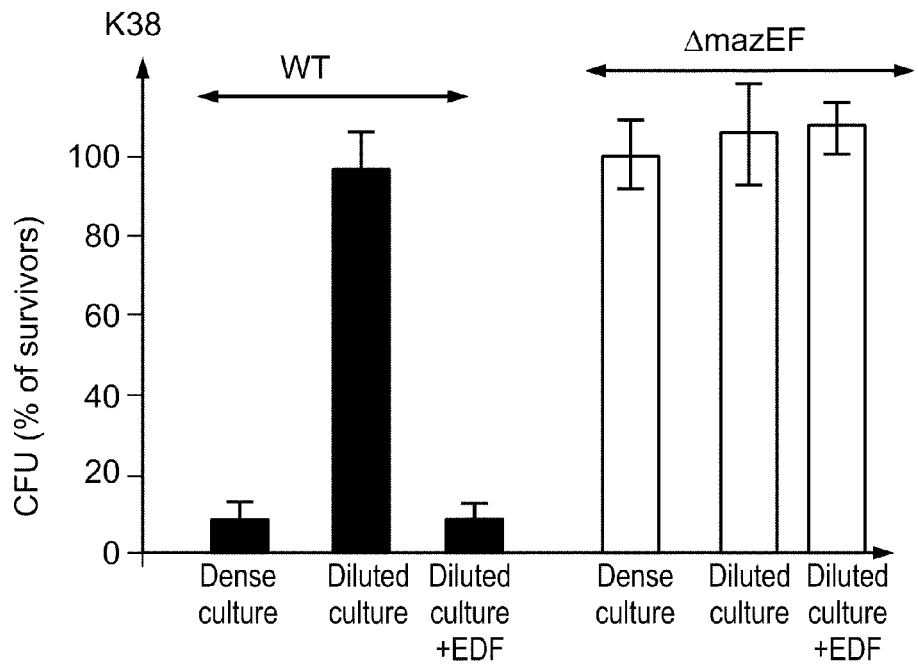
Figure 12C:
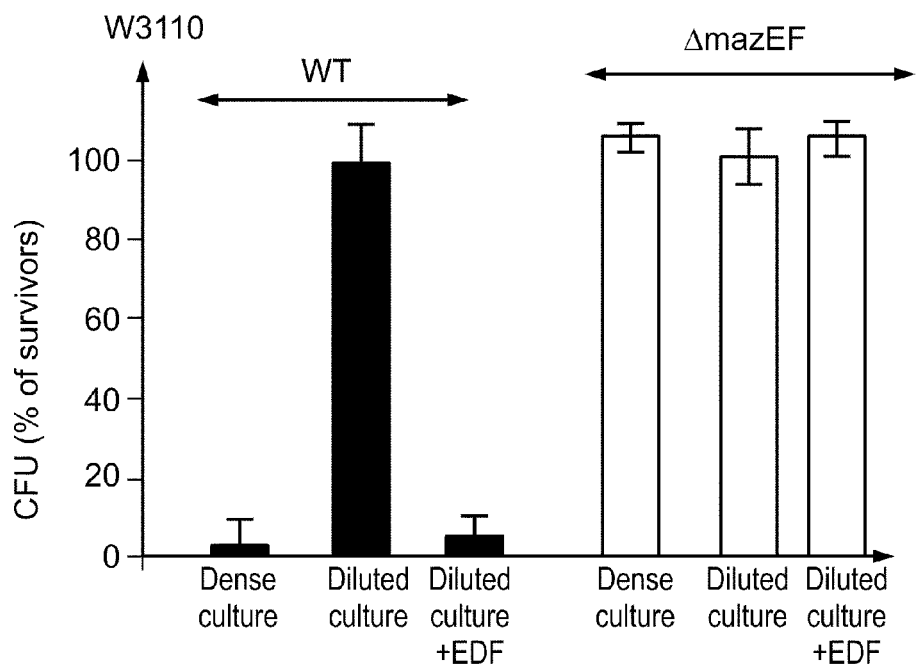

Fragmentation analysis (MS/MS) of the material from this 661 Dalton peak revealed that EDF is a linear peptide with an amino acid sequence Asn-Asn-Trp-Asn-Asn (NNWNN— SEQ ID NO: 1) FIG. 10B. The four Asn residues in EDF are vulnerable to deamidation under acidic conditions normally used for ESI-MS. The structure was verified by NMR analysis (FIG. 10C).

Figure 13A:
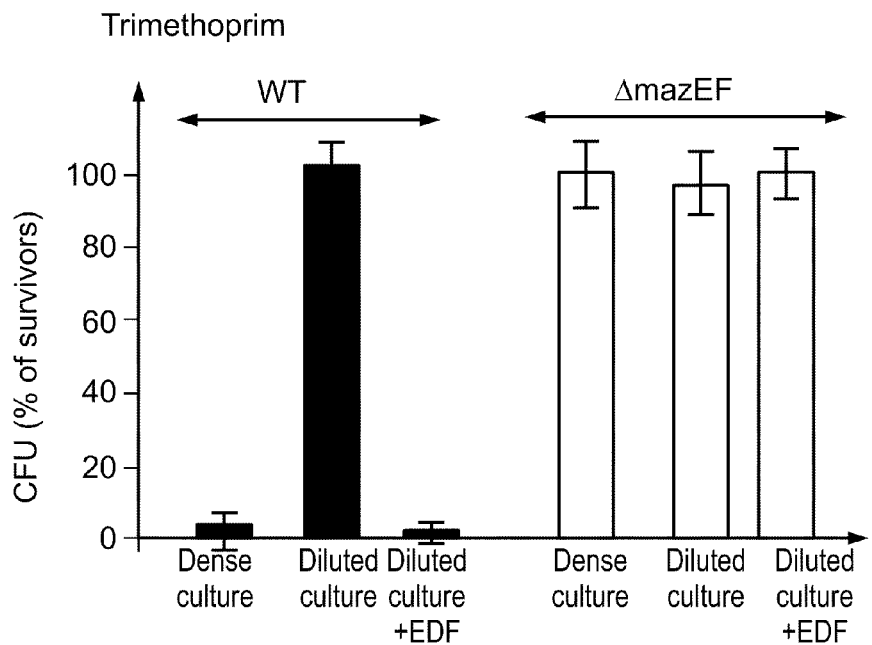
FIGS. 13A-B are bar graphs illustrating that the chemically synthesized EDF can restore mazEF mediated cell death to a diluted culture of MC4100relA$^+$ E. coli induced by trimothoprim (FIG. 13A) or chloramphenicol (FIG. 13B).
Figure 13B:
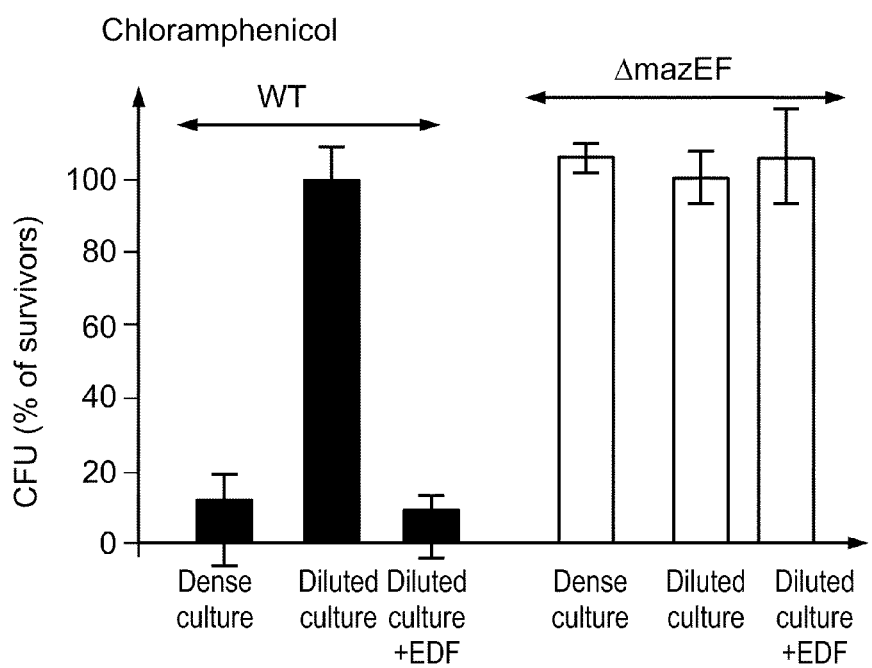

To test whether NNWNN peptide is indeed EDF, it was chemically synthesized and tested for biological activity. When added to a diluted culture, the synthetic peptide enhanced mazEF-mediated cell death when induced in different E. Coli strains by rifampicin (FIGS. 12A-12C), by trimethoprim (FIG. 13A) and by chloramphenicol (FIG. 13B).

EXAMPLE 6

Structural-Activity-Relationship Study

Materials and Methods

E. coli mazEF-mediated cell death in the presence of synthesized wild type (WT) and mutated EDF. E. coli MC4100relA$^+$t(WT) and MC4100relA$^+$ΔmazEF (ΔmazEF) were grown for 12 hours in M9 medium with shaking (160 rpm). Then, cells were diluted 1:100 in M9 medium and were grown with shaking (160 rpm) at 37° C. to a mid-logarithmic phase (OD$_{600}$=0.6). Duplicate samples were removed from the cultures at a density of 2.5×10$^8$ (Dense), diluted in pre-heated M9 medium to the density of 3×10$^4$ (M9) or diluted in pre-heated M9 applied with 1 μg/ml of one of the synthesized EDFs (SEQ ID NOs: 1-6). The samples were incubated for 10 minutes at 37° C. without shaking. Then rifampicin (10 μg/ml) was added and the cells were incubated for 10 minutes without shaking. The cells were centrifuged in 14000 rpm for 5 minutes and washed in pre-heated saline. Then, the cells were diluted, plated on LB plates and incubated at 37° C. for 12 hours. Cell killing was calculated by comparing the number of the colony-forming ability of cells treated by stressful conditions to those of the cells that were not exposed to the treatment.

Ability of mutant EDF molecules to inhibit wild type EDF activity: Various concentration of chemically synthesized WT EDF (SEQ ID NO: 1) were added to diluted cultures of *E. Coli* NC4100relA+ containing a constant amount (50 ng/ml) of each of the mutated EDF described in Table 6. The Experiment was carried out as described herein above.

The effect of deletions of genes possibly encoding EDF: *E. coli* strains MC4100relA+ (WT), MC4100re/A+Δzwf (Δ zwf), MC4100re/A+Δydd (Δ ydd), MC4100re/A+ΔygeO (Δ ygeO), MC4100re/A+ΔidnD(Δ idnD), MC4100re/A+ΔasnA(Δ asnA) and MC4100re/A+ΔasnB (Δ asnB) serving as an EDF donor, were grown to mid-logarithmic phase. Supernatants of the untreated dense cultures were obtained as described earlier. In order to determine the EDF activity of the collected supernatants, MC4100re/A+wt serving as an EDF acceptor was grown to a mid-logarithmic phase. Duplicate samples were removed from the culture at a density of $2.5 \times 10^8$, and diluted in the pre-warmed (37° C.) supernatant colluced from the conor culture during various stages of growth.

Results

Figure 14A:
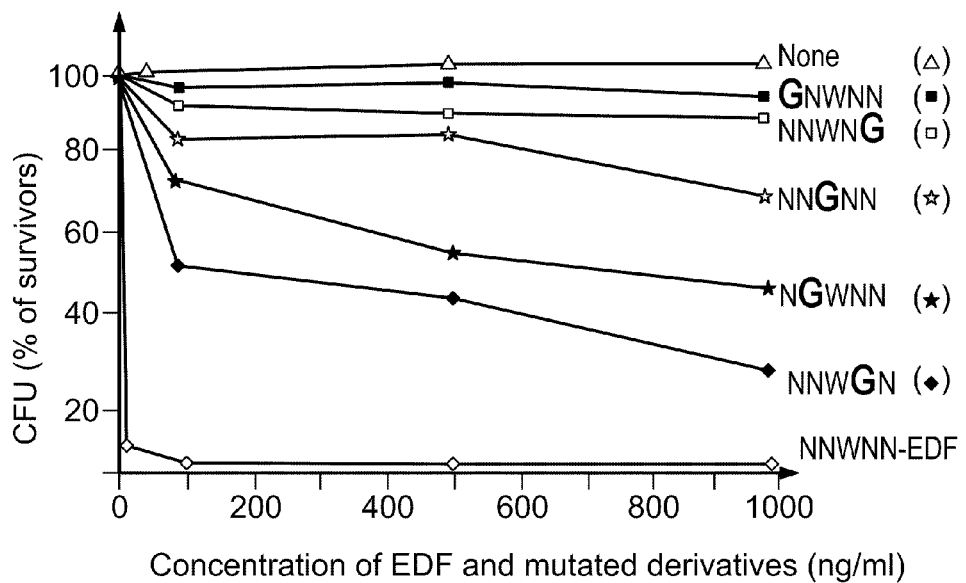
FIGS. 14A-B are graphs illustrating that NNWNN (SEQ ID NO: 1) is the optimal molecule for EDF activity.

Chemically synthesized EDF (NNWNN—SEQ ID NO: 1) of >98% purity was used. In order to determine whether each amino acid in peptide NNWNN (WT) is required for its killing activity, chemically synthesized artificial mutated peptides, each carrying a substitution of one of EDF's amino acids to glycine were generated. As shown in Table 6 herein below and FIG. 14A, changing the first and last amino acid prevented its killing activity. A moderate reduction in the killing activity was observed by changing the second, third, and fourth amino acid. Thus, each of the amino acids is important in the killing activity, and the external amino acids are the most crucial.

TABLE 6

| | % Cell killing following mazEF induction with rifampicin in response to 1 μg/ml of: | | | | | |
|---|---|---|---|---|---|---|
| No EDF | WT EDF- NNWNN (SEQ ID NO: 1) | Mutated EDF GNWNN (SEQ ID NO: 2) | Mutated EDF NGWNN (SEQ ID NO: 3) | Mutated EDF NNGNN (SEQ ID NO: 4) | Mutated EDF NNWGN (SEQ ID NO: 5) | Mutated EDF NNWNG (SEQ ID NO: 6) |
| 2 | 99.5 | 9 | 51 | 41 | 72 | 19 |

A similar hierarchy of amino acid importance was obtained when the ability of mutant EDF molecules to inhibit wild type EDF activity was examined (FIG. 15). Thus, EDF-s mutated at the terminal amino acids (1 and 5) were efficient inhibitors of EDF activity; however mutated EDF peptides in which glycine replaced the amino acids in positions 2, 3 or 4 inhibited EDF activity only when the concentration of wild-type EDF was low. These results indicate that amino acids 1 and 5 have roles similar to each other and amino acids 2-4 also have roles similar to each other.

Figure 14B:
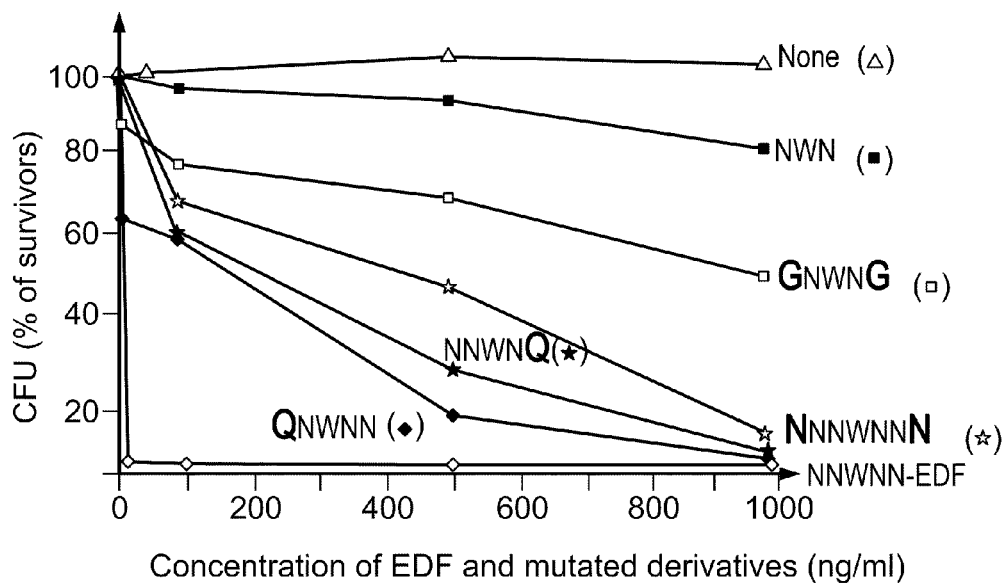

Examination of characteristics of EDF required for its activity revealed that (i) the tripeptide NWN (SEQ ID NO: 7) does not have EDF activity whereas the heptapeptide NNNWNNN (SEQ ID NO: 8) has partial activity; (ii) the presence of an amide at the external positions probably has a role in EDF activity, as the replacement of Asn by Gln (O) at either end of the pentapeptide (QNWNN—SEQ ID NO: 9, or NNWNQ—SEQ ID NO: 10) that is, a substitution that carries an amide and is structurally related to Asn led to only a partial reduction in EDF activity (FIG. 14B).

Using database analysis, the *E. coli* genome was searched for DNA sequences corresponding to the amino acid sequence NNWNN. Only five open reading frames predicted peptide similarity to NNWNN (as illustrated in Table 7 herein below).

TABLE 7

| Gene | Peptide sequence | Protein encoded by the gene | Accession Number (NCBI database) |
|---|---|---|---|
| zwf | NNWDN SEQ ID NO: 12 | Glucose-6-phosphate 1-dehydrogenase | AP_002472 |
| yddA | NDWNN SEQ ID NO: 14 | Fused predicted multidrug transporter subunits of ABC superfamily | AP_002119 |
| ygeO | NNWN SEQ ID NO: 13 | Hypothetical protein b2859 | AP_003420 |
| idnD | DWNN SEQ ID NO: 15 | L-idonate 5-dehydrogenase, NAD-binding | AP_004763 |
| ybaT | DWNN SEQ ID NO: 15 | Rac prophage; predicted protein | AP_001135 |

Table 7 summarizes a database search for genes that may encode the pentapeptide NNWNN. The pentapeptide NNWNN was searched against the translated ORFs of *E. coli* K12 and *E. coli* W3110 using BLAST. The search was done with adapted parameters for short sequences (allowing Expect value=1000).

Figure 16:
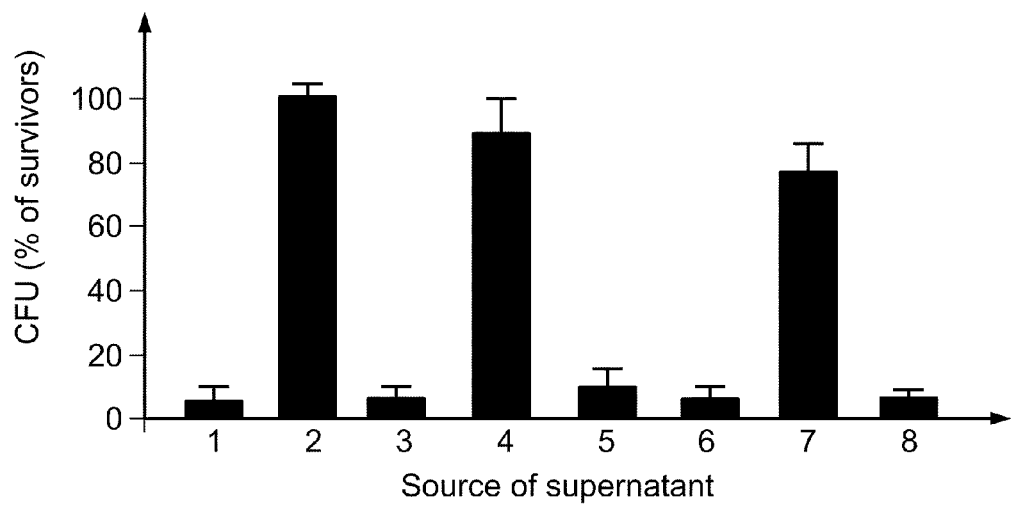
FIG. 16 is a bar graph illustrating the effect of deletions of genes possible encoding EDF.

The deletion of only two genes prevented the production of an active EDF (FIG. 16); zwf encoding NNWDN (SEQ ID NO: 12) (D=Asp) and ygeO encoding NNWN (SEQ ID NO: 13). The zwf product carrying the sequence NNWDN may be the precursor of EDF, and a subsequent amidation step may generate the full NNWNN sequence. Amidation may occur either before or after the cleavage of the precursor by one of the *E. Coli* proteases. Deletion of the gene Asn syntetase A (asnA) prevented production of active EDF, whereas deleting asnB (encoding Asn synthetase B) did not (FIG. 16). The product of the ygeO gene is also involved in the generation of EDF (FIG. 16).

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

What is claimed is:

1. A method of killing bacteria which comprise the mazEF toxin-antitoxin module and which are in logarithmic growth, the method comprising contacting the bacteria with an effective amount of an isolated pentapeptide, comprising a consensus amino acid sequence $X_1X_2X_3X_4X_5$, wherein both $X_1$ and $X_5$ comprise an amino acid independently selected from the group consisting of an asparagine residue and a glutamine residue wherein $X_3$ is a tryptophan residue and wherein $X_2$ and $X_4$ are each independently selected from the group consisting of an asparagine residue and a glycine residue, thereby killing bacteria.

2. The method of claim 1, having an amino acid sequence as set forth in SEQ ID NO: 1.

3. The method of claim 1, wherein the bacteria is of the genus *Bacillus* or *Escherichia*.

4. The method of claim 1, wherein the bacteria are additionally contacted with at least one agent capable of reducing a level of MazE selected from the group consisting of an antibiotic, a DNA damaging agent and a serine analogue.

* * * * *

SEQUENCE LISTING

<160> NUMBER OF SEQ ID NOS: 15

<210> SEQ ID NO 1
<211> LENGTH: 5
<212> TYPE: PRT
<213> ORGANISM: Artificial sequence
<220> FEATURE:
<223> OTHER INFORMATION: Chemically synthesized WT EDF

<400> SEQUENCE: 1

Asn Asn Trp Asn Asn
1 5

<210> SEQ ID NO 2
<211> LENGTH: 5
<212> TYPE: PRT
<213> ORGANISM: Artificial sequence
<220> FEATURE:
<223> OTHER INFORMATION: Chemically synthesized mutant EDF derivative

<400> SEQUENCE: 2

Gly Asn Trp Asn Asn
1 5

<210> SEQ ID NO 3
<211> LENGTH: 5
<212> TYPE: PRT
<213> ORGANISM: Artificial sequence
<220> FEATURE:
<223> OTHER INFORMATION: Chemically synthesized mutant EDF derivative

<400> SEQUENCE: 3

Asn Gly Trp Asn Asn
1 5

<210> SEQ ID NO 4
<211> LENGTH: 5
<212> TYPE: PRT
<213> ORGANISM: Artificial sequence
<220> FEATURE:
<223> OTHER INFORMATION: Chemically synthesized mutant EDF derivative

<400> SEQUENCE: 4

Asn Asn Gly Asn Asn
1 5

<210> SEQ ID NO 5
<211> LENGTH: 5
<212> TYPE: PRT
<213> ORGANISM: Artificial sequence
<220> FEATURE:
<223> OTHER INFORMATION: Chemically synthesized mutant EDF derivative

<400> SEQUENCE: 5

Asn Asn Trp Gly Asn
1 5

<210> SEQ ID NO 6
<211> LENGTH: 5
<212> TYPE: PRT
<213> ORGANISM: Artificial sequence
<220> FEATURE:
<223> OTHER INFORMATION: Chemically synthesized modified EDF derivative

<400> SEQUENCE: 6

Asn Asn Trp Asn Gly
1 5

```
<210> SEQ ID NO 7
<211> LENGTH: 3
<212> TYPE: PRT
<213> ORGANISM: Artificial sequence
<220> FEATURE:
<223> OTHER INFORMATION: Chemically synthesized modified EDF derivative

<400> SEQUENCE: 7

Asn Trp Asn
1

<210> SEQ ID NO 8
<211> LENGTH: 7
<212> TYPE: PRT
<213> ORGANISM: Artificial sequence
<220> FEATURE:
<223> OTHER INFORMATION: Chemically synthesized modified EDF derivative

<400> SEQUENCE: 8

Asn Asn Asn Trp Asn Asn Asn
1               5

<210> SEQ ID NO 9
<211> LENGTH: 5
<212> TYPE: PRT
<213> ORGANISM: Artificial sequence
<220> FEATURE:
<223> OTHER INFORMATION: Chemically synthesized modified EDF derivative

<400> SEQUENCE: 9

Gln Asn Trp Asn Asn
1               5

<210> SEQ ID NO 10
<211> LENGTH: 5
<212> TYPE: PRT
<213> ORGANISM: Artificial sequence
<220> FEATURE:
<223> OTHER INFORMATION: Chemically synthesized modified EDF derivative

<400> SEQUENCE: 10

Asn Asn Trp Asn Gln
1               5

<210> SEQ ID NO 11
<211> LENGTH: 5
<212> TYPE: PRT
<213> ORGANISM: Artificial sequence
<220> FEATURE:
<223> OTHER INFORMATION: Chemically synthesized modified EDF derivative

<400> SEQUENCE: 11

Gly Asn Trp Asn Gly
1               5

<210> SEQ ID NO 12
<211> LENGTH: 5
<212> TYPE: PRT
<213> ORGANISM: Escherichia coli
<220> FEATURE:
<221> NAME/KEY: misc_feature
<223> OTHER INFORMATION: A portion of an E. coli ORF having similarity
      to the EDF pentapeptide

<400> SEQUENCE: 12

Asn Asn Trp Asp Asn
```

```
<210> SEQ ID NO 13
<211> LENGTH: 4
<212> TYPE: PRT
<213> ORGANISM: Escherichia coli
<220> FEATURE:
<221> NAME/KEY: misc_feature
<223> OTHER INFORMATION: A portion of an E. coli ORF having similarity
      to the EDF pentapeptide

<400> SEQUENCE: 13

Asn Asn Trp Asn
1

<210> SEQ ID NO 14
<211> LENGTH: 5
<212> TYPE: PRT
<213> ORGANISM: Escherichia coli
<220> FEATURE:
<221> NAME/KEY: misc_feature
<223> OTHER INFORMATION: A portion of an E. coli ORF having similarity
      to the EDF pentapeptide

<400> SEQUENCE: 14

Asn Asp Trp Asn Asn
1               5

<210> SEQ ID NO 15
<211> LENGTH: 4
<212> TYPE: PRT
<213> ORGANISM: Escherichia coli
<220> FEATURE:
<221> NAME/KEY: misc_feature
<223> OTHER INFORMATION: A portion of an E. coli ORF having similarity
      to the EDF pentapeptide

<400> SEQUENCE: 15

Asp Trp Asn Asn
1
```